(12) United States Patent
Jucovic et al.

(10) Patent No.: US 11,384,125 B2
(45) Date of Patent: Jul. 12, 2022

(54) EXPRESSION CASSETTE AND HOST CELL FOR EXPRESSING A VIP3-INTERACTING PROTEIN

(71) Applicant: Syngenta Crop Protection AG, Basel (CH)

(72) Inventors: Milan Jucovic, Research Triangle Park, NC (US); Renshui Liu, Research Triangle Park, NC (US); Richard Sessler, Research Triangle Park, NC (US); Guo-Qing Tang, Research Triangle Park, NC (US); Jeng Shong Chen, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 75 days.

(21) Appl. No.: 17/066,826

(22) Filed: Oct. 9, 2020

(65) Prior Publication Data

US 2021/0024592 A1    Jan. 28, 2021

Related U.S. Application Data

(62) Division of application No. 16/100,824, filed on Aug. 10, 2018, now Pat. No. 10,836,801, which is a division of application No. 15/120,563, filed as application No. PCT/EP2015/054100 on Feb. 26, 2015, now abandoned.

(60) Provisional application No. 61/945,454, filed on Feb. 27, 2014.

(51) Int. Cl.

| | |
|---|---|
| *C12N 9/14* | (2006.01) |
| *C12N 5/10* | (2006.01) |
| *C07K 14/435* | (2006.01) |
| *C12N 15/82* | (2006.01) |
| *A01N 37/46* | (2006.01) |
| *G01N 33/68* | (2006.01) |
| *A01N 63/50* | (2020.01) |
| *C12N 15/10* | (2006.01) |
| *G01N 33/566* | (2006.01) |

(52) U.S. Cl.
CPC ........ *C07K 14/43563* (2013.01); *A01N 37/46* (2013.01); *A01N 63/50* (2020.01); *C12N 9/14* (2013.01); *C12N 15/1037* (2013.01); *C12N 15/8286* (2013.01); *G01N 33/566* (2013.01); *G01N 33/68* (2013.01); *G01N 2333/705* (2013.01); *G01N 2430/10* (2013.01); *G01N 2500/04* (2013.01); *Y02A 40/146* (2018.01)

(58) Field of Classification Search
None
See application file for complete search history.

(56) References Cited

U.S. PATENT DOCUMENTS 5,877,012 A    3/1999   Estruch et al.

OTHER PUBLICATIONS

Singh, G. et al., Applied and Environmental Microbiology, vol. 76, No. 21, Nov. 2010, 7202-7209.
Bergamasco et al., Journal of Invertebrate Pathology, vol. 112, No. 2, Feb. 1, 2013, 152-158.
He, Molecular Plant, vol. 2, No. 4, Jul. 1, 2009, 554-564.
Database accession No. K9RZR5 sequence, retrieved from EBI accession No. UNIPROT:K9RZR5, Mar. 6, 2013.
Database accession No. S5FXH1 sequence, retrieved from EBI accession No. UNIPROT:S5FXH1, Oct. 16, 2013.
Database accession No. H6T598 sequence, retrieved from EBI accession No. UNIPROT:H6I598, Apr. 18, 2012.
Database accession No. E2GHX4 sequence, retrieved from EBI accession No. UNIPROT: E2GHX4, Nov. 30, 2010.
Database accession No. Q2F513 sequence, retrieved from EBI accession No. UNIPROT: Q2F5T3, Mar. 21, 2006.
International Search Report dated May 27, 2015 for International Application No. PCT/EP2015/054100.
Database accession No. Q2F5J2 sequence, retrieved from EBI accession No. UNIPROT: Q2F5J2, Mar. 21, 2003.

*Primary Examiner* — David Steadman
(74) *Attorney, Agent, or Firm* — Katherine Seguin

(57) ABSTRACT

This invention provides polypeptides that were identified as interacting with Vip3 toxin. This invention also provides a method of identifying agents that bind to Vip3 interacting polypeptides, which agents may act as insecticidal agent, cytotoxic agents and/or modulate the activity of Vip3 interacting polypeptides.

15 Claims, No Drawings
Specification includes a Sequence Listing.

SEQUENCE LISTING

<160> NUMBER OF SEQ ID NOS: 11

<210> SEQ ID NO 1
<211> LENGTH: 556
<212> TYPE: PRT
<213> ORGANISM: Spodoptera frugiperda

<400> SEQUENCE: 1

-continued

```
Met Ser Leu Ile Ser Ala Arg Ile Ala Gly Ser Val Ala Arg Leu
1               5                   10                  15
Pro Asn Ala Ala Ser Gln Val Ser Lys Val Ala Gly Val Ala Pro
                20                  25                  30
Ala Val Ala Val Ala Ser Arg Asn Phe His Val Ser Pro Thr Gln Lys
            35                  40                  45
Ala Ala Glu Ile Ser Thr Ile Leu Glu Glu Arg Ile Leu Gly Ala Ala
50                      55                  60
Pro Lys Ala Asp Leu Glu Thr Gly Arg Val Leu Ser Ile Gly Asp
65                  70                  75                  80
Gly Ile Ala Arg Val Tyr Gly Leu Lys Asn Ile Gln Ala Glu Glu Met
                85                  90                  95
Val Glu Phe Ser Ser Gly Leu Lys Gly Met Ala Leu Asn Leu Glu Pro
                100                 105                 110
Asp Asn Val Gly Val Val Phe Gly Asn Asp Lys Leu Ile Lys Glu
                115                 120                 125
Gly Asp Ile Val Lys Arg Thr Gly Ala Ile Val Asp Val Pro Val Gly
            130                 135                 140
Glu Gln Leu Leu Gly Arg Val Val Asp Ala Leu Gly Asn Ala Ile Asp
145                 150                 155                 160
Gly Lys Gly Pro Ile Asp Thr Lys Ser Arg Met Arg Val Gly Ile Lys
                165                 170                 175
Ala Pro Gly Ile Ile Pro Arg Val Ser Val Arg Glu Pro Met Gln Thr
                180                 185                 190
Gly Ile Lys Ala Val Asp Ser Leu Val Pro Ile Gly Arg Gly Gln Arg
                195                 200                 205
Glu Leu Ile Ile Gly Asp Arg Gln Thr Gly Lys Thr Ala Leu Ala Ile
            210                 215                 220
Asp Thr Ile Ile Asn Gln Gln Arg Phe Asn Lys Gly Gln Asp Glu Lys
225                 230                 235                 240
Lys Lys Leu Tyr Cys Ile Tyr Val Ala Ile Gly Gln Lys Arg Ser Thr
                245                 250                 255
Val Ala Gln Ile Val Lys Arg Leu Thr Asp Ala Gly Ala Ile Asn Tyr
                260                 265                 270
Thr Ile Ile Val Ser Arg Thr Ala Ser Asp Ala Ala Pro Leu Gln Tyr
                275                 280                 285
Leu Ala Pro Tyr Ser Gly Cys Ala Met Gly Glu Phe Phe Arg Asp Asn
                290                 295                 300
Gly Lys His Ala Leu Ile Ile Tyr Asp Asp Leu Ser Lys Gln Ala Val
305                 310                 315                 320
Ala Tyr Arg Gln Met Ser Leu Leu Leu Arg Arg Pro Pro Gly Arg Glu
                325                 330                 335
Ala Tyr Pro Gly Asp Val Phe Tyr Leu His Ser Arg Leu Leu Glu Arg
                340                 345                 350
Ala Ala Lys Met Ser Asp Lys Met Gly Gly Gly Ser Leu Thr Ala Leu
                355                 360                 365
Pro Val Ile Glu Thr Gln Ala Gly Asp Val Ser Ala Tyr Ile Pro Thr
370                 375                 380
Asn Val Ile Ser Ile Thr Asp Gly Gln Ile Phe Leu Glu Thr Glu Leu
385                 390                 395                 400
Phe Tyr Lys Gly Ile Arg Pro Ala Ile Asn Val Gly Leu Ser Val Ser
                405                 410                 415
Arg Val Gly Ser Ala Ala Gln Thr Lys Ala Met Lys Gln Val Ala Gly
```

-continued

```
                420             425             430
Ser Met Lys Leu Glu Leu Ala Gln Tyr Arg Glu Val Ala Ala Phe Ala
            435             440             445

Gln Phe Gly Ser Asp Leu Asp Ala Ala Thr Gln Gln Leu Leu Asn Arg
            450             455             460

Gly Met Arg Leu Thr Glu Leu Leu Lys Gln Gly Gln Tyr Val Pro Met
465             470             475             480

Ala Ile Glu Glu Gln Val Ala Ile Ile Tyr Cys Gly Val Arg Gly His
            485             490             495

Leu Asp Lys Leu Asp Pro Ser Lys Ile Thr Gly Phe Glu Lys Glu Phe
            500             505             510

Thr Gln His Ile Lys Thr Ser His Gln Gly Leu Leu Ala Thr Ile Ala
            515             520             525

Lys Asp Gly Gln Ile Thr Pro Glu Ser Asp Ala Ala Leu Lys Lys Ile
            530             535             540

Val Thr Asp Phe Leu Ala Thr Phe Thr Gln Ser Gln
545             550             555

<210> SEQ ID NO 2
<211> LENGTH: 516
<212> TYPE: PRT
<213> ORGANISM: Spodoptera frugiperda

<400> SEQUENCE: 2

Met Val Gly Ala Ile Ser Arg Val Gly Ser Gly Ile Leu Ala Val Lys
1               5               10              15

Ser Val Ala Glu Lys Thr Leu Thr Glu Cys Gly Lys Ile Ala Thr Val
            20              25              30

Ser Ala Ile Asn Lys Arg Asp Tyr Ala Lys Ala Ala Gly Lys Gly
            35              40              45

Gln Gly Lys Val Val Ala Val Ile Gly Ala Val Val Asp Val Gln Phe
        50              55              60

Glu Asp Asn Leu Pro Pro Ile Leu Asn Ala Leu Glu Val Gln Asn Arg
65              70              75              80

Gln Pro Arg Leu Val Leu Glu Val Ala Gln His Leu Gly Glu Asn Thr
            85              90              95

Val Arg Thr Ile Ala Met Asp Gly Thr Glu Gly Leu Val Arg Gly Gln
            100             105             110

Pro Val Leu Asp Cys Gly Ser Pro Ile Arg Ile Pro Val Gly Ala Glu
            115             120             125

Thr Leu Gly Arg Ile Ile Asn Val Ile Gly Glu Pro Ile Asp Glu Arg
            130             135             140

Gly Pro Ile Pro Thr Asp Lys Thr Ala Ala Ile His Ala Glu Ala Pro
145             150             155             160

Glu Phe Val Asp Met Ser Val Gln Gln Glu Ile Leu Val Thr Gly Ile
            165             170             175

Lys Val Val Asp Leu Leu Ala Pro Tyr Ala Lys Gly Gly Lys Ile Gly
            180             185             190

Leu Phe Gly Gly Ala Gly Val Gly Lys Thr Val Leu Ile Met Glu Leu
            195             200             205

Ile Asn Asn Val Ala Lys Ala His Gly Gly Tyr Ser Val Phe Ala Gly
            210             215             220

Val Gly Glu Arg Thr Arg Glu Gly Asn Asp Leu Tyr His Glu Met Ile
225             230             235             240
```

-continued

Glu Ser Gly Val Ile Ser Leu Lys Asp Lys Thr Ser Lys Val Ala Leu
                245                 250                 255

Val Tyr Gly Gln Met Asn Glu Pro Pro Gly Ala Arg Ala Arg Val Ala
            260                 265                 270

Leu Thr Gly Leu Thr Val Ala Glu Tyr Phe Arg Asp Gln Glu Gly Gln
        275                 280                 285

Asp Val Leu Leu Phe Ile Asp Asn Ile Phe Arg Phe Thr Gln Ala Gly
    290                 295                 300

Ser Glu Val Ser Ala Leu Leu Gly Arg Ile Pro Ser Ala Val Gly Tyr
305                 310                 315                 320

Gln Pro Thr Leu Ala Thr Asp Met Gly Thr Met Gln Glu Arg Ile Thr
                325                 330                 335

Thr Thr Lys Lys Gly Ser Ile Thr Ser Val Gln Ala Ile Tyr Val Pro
            340                 345                 350

Ala Asp Asp Leu Thr Asp Pro Ala Pro Ala Thr Thr Phe Ala His Leu
        355                 360                 365

Asp Ala Thr Thr Val Leu Ser Arg Ala Ile Ala Glu Leu Gly Ile Tyr
    370                 375                 380

Pro Ala Val Asp Pro Leu Asp Ser Thr Ser Arg Ile Met Asp Pro Asn
385                 390                 395                 400

Ile Ile Gly Ala Glu His Tyr Asn Val Ala Arg Gly Val Gln Lys Ile
                405                 410                 415

Leu Gln Asp Tyr Lys Ser Leu Gln Asp Ile Ile Ala Ile Leu Gly Met
            420                 425                 430

Asp Glu Leu Ser Glu Glu Asp Lys Leu Thr Val Ala Arg Ala Arg Lys
        435                 440                 445

Ile Gln Arg Phe Leu Ser Gln Pro Phe Gln Val Ala Glu Val Phe Thr
    450                 455                 460

Gly His Ala Gly Lys Leu Val Pro Leu Glu Glu Thr Ile Lys Gly Phe
465                 470                 475                 480

Ser Lys Ile Leu Gln Gly Glu Tyr Asp His Leu Pro Glu Val Ala Phe
                485                 490                 495

Tyr Met Val Gly Pro Ile Glu Glu Val Val Ala Lys Ala Asp Thr Leu
            500                 505                 510

Ala Lys Asn Ala
        515

<210> SEQ ID NO 3
<211> LENGTH: 654
<212> TYPE: PRT
<213> ORGANISM: Spodoptera frugiperda

<400> SEQUENCE: 3

Met Ala Ala Thr Lys Ala Pro Ala Val Gly Ile Asp Leu Gly Thr Thr
1               5                   10                  15

Tyr Ser Cys Val Gly Val Phe Gln His Gly Lys Val Glu Ile Ile Ala
            20                  25                  30

Asn Asp Gln Gly Asn Arg Thr Thr Pro Ser Tyr Val Ala Phe Thr Asp
        35                  40                  45

Thr Glu Arg Leu Ile Gly Asp Ala Ala Lys Asn Gln Val Ala Met Asn
    50                  55                  60

Pro Asn Asn Thr Ile Phe Asp Ala Lys Arg Leu Ile Gly Arg Lys Phe
65                  70                  75                  80

Glu Asp Ala Thr Val Gln Ala Asp Met Lys His Trp Pro Phe Glu Val
                85                  90                  95

```
Val Ser Asp Gly Gly Lys Pro Lys Ile Lys Val Ser Tyr Lys Gly Glu
            100                 105                 110

Asp Lys Thr Phe Phe Pro Glu Glu Val Ser Ser Met Val Leu Thr Lys
            115                 120                 125

Met Lys Glu Thr Ala Glu Ala Tyr Leu Gly Lys Thr Val Gln Asn Ala
            130                 135                 140

Val Ile Thr Val Pro Ala Tyr Phe Asn Asp Ser Gln Arg Gln Ala Thr
145                 150                 155                 160

Lys Asp Ala Gly Thr Ile Ser Gly Leu Asn Val Leu Arg Ile Ile Asn
                    165                 170                 175

Glu Pro Thr Ala Ala Ile Ala Tyr Gly Leu Asp Lys Lys Gly Ser
                180                 185                 190

Gly Glu Arg Asn Val Leu Ile Phe Asp Leu Gly Gly Gly Thr Phe Asp
                195                 200                 205

Val Ser Ile Leu Thr Ile Glu Asp Gly Ile Phe Glu Val Lys Ser Thr
            210                 215                 220

Ala Gly Asp Thr His Leu Gly Gly Glu Asp Phe Asp Asn Arg Met Val
225                 230                 235                 240

Asn His Phe Val Gln Glu Phe Lys Arg Lys Tyr Lys Lys Asp Leu Ala
                    245                 250                 255

Thr Asn Lys Arg Ala Leu Arg Arg Leu Arg Thr Ala Cys Glu Arg Ala
                260                 265                 270

Lys Arg Thr Leu Ser Ser Ser Thr Gln Ala Ser Ile Glu Ile Asp Ser
            275                 280                 285

Leu Phe Glu Gly Ile Asp Phe Tyr Thr Ser Ile Thr Arg Ala Arg Phe
            290                 295                 300

Glu Glu Leu Asn Ala Asp Leu Phe Arg Ser Thr Met Glu Pro Val Glu
305                 310                 315                 320

Lys Ser Leu Arg Asp Arg Lys Met Asp Lys Ser Gln Ile His Asp Ile
                    325                 330                 335

Val Leu Val Gly Gly Ser Thr Arg Ile Pro Lys Val Gln Lys Leu Leu
                340                 345                 350

Gln Asp Phe Phe Asn Gly Lys Glu Leu Asn Lys Ser Ile Asn Pro Asp
            355                 360                 365

Glu Ala Val Ala Tyr Gly Ala Ala Val Gln Ala Ala Ile Leu His Gly
            370                 375                 380

Asp Lys Ser Glu Glu Val Gln Asp Leu Leu Leu Leu Asp Val Thr Pro
385                 390                 395                 400

Leu Ser Leu Gly Ile Glu Thr Ala Gly Gly Val Met Thr Thr Leu Ile
                    405                 410                 415

Lys Arg Asn Thr Thr Ile Pro Thr Lys Gln Thr Gln Thr Phe Thr Thr
                420                 425                 430

Tyr Ser Asp Asn Gln Pro Gly Val Leu Ile Gln Val Phe Glu Gly Glu
            435                 440                 445

Arg Ala Met Thr Lys Asp Asn Asn Leu Leu Gly Lys Phe Glu Leu Thr
            450                 455                 460

Gly Ile Pro Pro Ala Pro Arg Gly Val Pro Gln Ile Glu Val Thr Phe
465                 470                 475                 480

Asp Ile Asp Ala Asn Gly Ile Leu Asn Val Ser Ala Val Glu Lys Ser
                    485                 490                 495

Thr Asn Lys Glu Asn Lys Ile Thr Ile Thr Asn Asp Lys Gly Arg Leu
                500                 505                 510
```

```
Ser Lys Glu Glu Ile Glu Arg Met Val Asn Glu Ala Glu Lys Tyr Arg
            515                 520                 525

Thr Glu Asp Glu Lys Gln Lys Glu Thr Ile Gln Ala Lys Asn Ala Leu
        530                 535                 540

Glu Ser Tyr Cys Phe Asp Met Lys Ser Thr Met Glu Asp Glu Lys Leu
545                 550                 555                 560

Lys Asp Lys Ile Ser Asp Ser Asp Lys Gln Thr Ile Leu Asp Lys Cys
                565                 570                 575

Asn Asp Thr Ile Lys Trp Leu Asp Ser Asn Gln Leu Ala Asp Lys Glu
            580                 585                 590

Glu Tyr Glu His Lys Gln Lys Glu Leu Glu Gly Ile Cys Asn Pro Ile
        595                 600                 605

Ile Thr Lys Met Tyr Gln Gly Ala Gly Gly Met Pro Gly Gly Met Pro
    610                 615                 620

Gly Gly Met Pro Gly Phe Pro Gly Gly Ala Pro Gly Ala Gly Gly Ala
625                 630                 635                 640

Ala Pro Gly Gly Gly Ala Gly Pro Thr Ile Glu Glu Val Asp
                645                 650

<210> SEQ ID NO 4
<211> LENGTH: 274
<212> TYPE: PRT
<213> ORGANISM: Helicoverpa zea

<400> SEQUENCE: 4

Met Ala Ala Gln Leu Phe Asn Arg Ile Gly Gln Val Gly Leu Gly Val
1               5                   10                  15

Ala Leu Val Gly Gly Val Val Asn Ser Ala Leu Tyr Asn Val Asp Gly
            20                  25                  30

Gly His Arg Ala Val Ile Phe Asp Arg Phe Ala Gly Val Lys Asn Leu
        35                  40                  45

Val Val Gly Glu Gly Thr His Phe Phe Val Pro Trp Val Gln Arg Pro
    50                  55                  60

Ile Ile Phe Asp Ile Arg Ser Arg Pro Arg Asn Val Pro Thr Val Thr
65                  70                  75                  80

Gly Ser Lys Asp Leu Gln Asn Val Asn Ile Thr Leu Arg Ile Leu Phe
                85                  90                  95

Arg Pro Ile Pro Asp Gln Leu Pro Lys Ile Tyr Thr Ile Leu Gly Ile
            100                 105                 110

Asp Tyr Asp Glu Arg Val Leu Pro Ser Ile Thr Ser Glu Val Leu Lys
        115                 120                 125

Ala Val Val Ala Gln Phe Asp Ala Gly Glu Leu Ile Thr Gln Arg Glu
    130                 135                 140

Val Val Ser Gln Lys Val Asn Glu Ser Leu Thr Glu Arg Ala Ala Gln
145                 150                 155                 160

Phe Gly Leu Ile Leu Asp Asp Ile Ser Ile Thr His Leu Thr Phe Gly
                165                 170                 175

Lys Glu Phe Thr Gln Ala Val Glu Leu Lys Gln Val Ala Gln Gln Glu
            180                 185                 190

Ala Glu Lys Ala Arg Phe Leu Val Glu Lys Ala Glu Gln Gln Lys Lys
        195                 200                 205

Ala Ala Val Ile Ala Ala Glu Gly Asp Ala Gln Ala Ala Val Leu Leu
    210                 215                 220

Ala Lys Ser Phe Gly Gln Ala Gly Glu Gly Leu Val Glu Pro Arg Arg
225                 230                 235                 240
```

Ile Glu Ala Ala Glu Asp Ile Ala Tyr Gln Leu Ser Lys Ser Arg Asn
            245                 250                 255

Val Thr Tyr Leu Pro Gln Gly Gln Asn Val Leu Leu Asn Leu Pro Thr
        260                 265                 270

Gln Asn

<210> SEQ ID NO 5
<211> LENGTH: 274
<212> TYPE: PRT
<213> ORGANISM: Manduca sexta

<400> SEQUENCE: 5

Met Ala Ala Gln Leu Phe Asn Arg Ile Gly Gln Val Gly Leu Gly Val
1               5                   10                  15

Ala Leu Val Gly Gly Val Val Asn Ser Ala Leu Tyr Asn Val Asp Gly
            20                  25                  30

Gly His Arg Ala Val Ile Phe Asp Arg Phe Ala Gly Val Lys Asn Met
        35                  40                  45

Val Val Gly Glu Gly Thr His Phe Phe Ile Pro Trp Val Gln Arg Pro
    50                  55                  60

Ile Ile Phe Asp Ile Arg Ser Arg Pro Arg Asn Val Pro Thr Ile Thr
65                  70                  75                  80

Gly Ser Lys Asp Leu Gln Asn Val Asn Ile Thr Leu Arg Ile Leu Phe
                85                  90                  95

Arg Pro Val Pro Asp Glu Leu Pro Arg Ile Tyr Thr Ile Leu Gly Val
            100                 105                 110

Asp Tyr Asp Glu Arg Val Leu Pro Ser Ile Thr Ser Glu Val Leu Lys
        115                 120                 125

Ala Val Val Ala Gln Phe Asp Ala Gly Glu Leu Ile Thr Gln Arg Glu
    130                 135                 140

Val Val Ser Gln Lys Val Asn Glu Ser Leu Thr Glu Arg Ala Gly Gln
145                 150                 155                 160

Phe Gly Leu Ile Leu Asp Asp Ile Ser Ile Thr His Leu Thr Phe Gly
                165                 170                 175

Lys Glu Phe Thr Gln Ala Val Glu Leu Lys Gln Val Ala Gln Gln Glu
            180                 185                 190

Ala Glu Lys Ala Arg Phe Leu Val Glu Lys Ala Glu Gln Gln Lys Lys
        195                 200                 205

Ala Ala Val Ile Ala Ala Glu Gly Asp Ala Gln Ala Ala Val Leu Leu
    210                 215                 220

Ala Lys Ser Phe Gly Ser Ala Gly Glu Gly Leu Val Glu Leu Arg Arg
225                 230                 235                 240

Ile Glu Ala Ala Glu Asp Ile Ala Tyr Gln Leu Ser Lys Ser Arg Asn
                245                 250                 255

Val Thr Tyr Leu Pro Gln Gly Gln Asn Val Leu Leu Asn Leu Pro Thr
            260                 265                 270

Gln Asn

<210> SEQ ID NO 6
<211> LENGTH: 299
<212> TYPE: PRT
<213> ORGANISM: Helicoverpa zea

<400> SEQUENCE: 6

Met Ala Gln Ser Lys Ile Asn Asp Met Ala Gly Lys Phe Ala Lys Gly

```
            1               5                   10                  15
          Gly Pro Pro Gly Leu Asn Ala Gly Leu Lys Val Ala Val Val Gly
                          20                  25                  30

Ala Ala Ala Tyr Gly Ile Ser Gln Ser Leu Phe Thr Val Glu Gly Gly
                          35                  40                  45

His Arg Ala Ile Met Phe Asn Arg Ile Gly Gly Ile Gln Gln His Val
              50                  55                  60

Met Ser Glu Gly Met His Phe Arg Ile Pro Trp Phe Gln Tyr Pro Ile
          65                  70                  75                  80

Ile Tyr Asp Ile Arg Ser Arg Pro Arg Lys Ile Ser Ser Pro Thr Gly
                          85                  90                  95

Ser Lys Asp Leu Gln Met Val Asn Ile Ser Leu Arg Val Leu Ser Arg
                          100                 105                 110

Pro Asp Ala Ser Ser Leu Pro Thr Met Tyr Arg Gln Leu Gly Thr Asp
                          115                 120                 125

Tyr Asp Glu Lys Val Leu Pro Ser Ile Cys Asn Glu Val Leu Lys Ser
                          130                 135                 140

Val Val Ala Lys Phe Asn Ala Ser Gln Leu Ile Thr Gln Arg Gln Gln
          145                 150                 155                 160

Val Ser Leu Leu Ile Arg Arg Glu Leu Val Glu Arg Ala Ala Asp Phe
                          165                 170                 175

Asn Ile Ile Leu Asp Asp Val Ser Leu Thr Glu Leu Ser Phe Gly Lys
                          180                 185                 190

Glu Tyr Thr Ala Ala Val Glu Ala Lys Gln Val Ala Gln Gln Glu Ala
                          195                 200                 205

Gln Arg Ala Ala Phe Val Val Glu Arg Ala Lys Gln Glu Arg Gln Gln
                          210                 215                 220

Lys Ile Val Gln Ala Glu Gly Glu Ala Glu Ala Glu Met Leu Gly
          225                 230                 235                 240

Lys Ala Met Gly Met Asn Pro Gly Tyr Leu Lys Leu Arg Lys Ile Arg
                          245                 250                 255

Ala Ala Gln Ser Ile Ser Arg Met Ile Ala Gln Ser Gln Asn Arg Val
                          260                 265                 270

Phe Leu Pro Gly Asn Ser Leu Met Ile Asn Leu Gln Asp Pro Thr Phe
                          275                 280                 285

Asp Asp Leu Ser Glu Lys Leu Thr Lys Lys Lys
                          290                 295

<210> SEQ ID NO 7
<211> LENGTH: 299
<212> TYPE: PRT
<213> ORGANISM: Manduca sexta

<400> SEQUENCE: 7

Met Ala Gln Ser Lys Ile Asn Asp Met Ala Gly Lys Phe Ala Lys Gly
          1               5                   10                  15

Gly Pro Pro Gly Leu Gly Ile Gly Leu Lys Val Val Ala Val Val Gly
                          20                  25                  30

Ala Ala Ala Tyr Gly Ile Ser Gln Ser Leu Tyr Thr Val Glu Gly Gly
                          35                  40                  45

His Arg Ala Ile Met Phe Asn Arg Ile Gly Gly Val Gln Gln His Val
              50                  55                  60

Met Ser Glu Gly Met His Phe Arg Val Pro Trp Phe Gln Tyr Pro Ile
          65                  70                  75                  80
```

```
Ile Tyr Asp Ile Arg Ser Arg Pro Arg Lys Ile Ser Ser Pro Thr Gly
                85                  90                  95

Ser Lys Asp Leu Gln Met Val Asn Ile Ser Leu Arg Val Leu Ser Arg
            100                 105                 110

Pro Asn Ser Ser Thr Leu Pro Thr Met Tyr Arg Gln Leu Gly Thr Asp
            115                 120                 125

Tyr Asp Glu Lys Val Leu Pro Ser Ile Cys Asn Glu Val Leu Lys Ser
        130                 135                 140

Val Val Ala Lys Phe Asn Ala Ser Gln Leu Ile Thr Gln Arg Gln Gln
145                 150                 155                 160

Val Ser Leu Leu Ile Arg Arg Glu Leu Val Glu Arg Ala Ala Asp Phe
                165                 170                 175

Asn Ile Ile Leu Asp Asp Val Ser Leu Thr Glu Leu Ser Phe Gly Lys
                180                 185                 190

Glu Tyr Thr Ala Ala Val Glu Ala Lys Gln Val Ala Gln Gln Glu Ala
            195                 200                 205

Gln Arg Ala Ala Phe Val Val Glu Arg Ala Lys Gln Glu Arg Gln Gln
        210                 215                 220

Lys Ile Val Gln Ala Glu Gly Glu Ala Glu Ala Glu Met Leu Gly
225                 230                 235                 240

Lys Ala Met Gly Met Asn Pro Gly Tyr Leu Lys Leu Arg Lys Ile Arg
                245                 250                 255

Ala Ala Gln Ser Ile Ser Arg Met Ile Ala Gln Ser Gln Asn Arg Val
                260                 265                 270

Phe Leu Pro Gly Asn Ser Leu Met Ile Asn Leu Gln Asp Pro Thr Phe
            275                 280                 285

Asp Asp Leu Ser Glu Lys Leu Thr Lys Lys Lys
        290                 295

<210> SEQ ID NO 8
<211> LENGTH: 373
<212> TYPE: PRT
<213> ORGANISM: Manduca sexta

<400> SEQUENCE: 8

Met Asp Ala Lys Ala Leu Ser Ser Ala Val Ala Lys Phe Ser Ala Lys
1               5                   10                  15

Phe Cys Asn Glu Leu Asp Lys Ser Lys Ser Val Val Ser Ser Pro Leu
                20                  25                  30

Ser Ala Glu Tyr Leu Leu Ala Leu Leu Ala Leu Gly Thr Thr Glu Pro
            35                  40                  45

Ala His Ser Glu Leu Leu Thr Ala Leu Asp Ile Pro Asp Asn Asp Ser
        50                  55                  60

Ile Arg Ser Ser Phe Gly Ala Val Ser Ala Lys Leu Lys Gly Ile Lys
65                  70                  75                  80

Gly Val Thr Phe Asn Val Ala Asn Lys Ile Tyr Ile Lys Asp Gly Gly
                85                  90                  95

Tyr Glu Leu Val Pro Glu Leu Lys Glu Asp Ala Glu Lys Val Phe Asp
            100                 105                 110

Ala Glu Phe Glu Lys Val Asp Phe Asp Asn Ser Ala Ala Ala Ala Asp
        115                 120                 125

Leu Ile Asn Lys Trp Val Glu Asn Lys Thr Asn Glu Lys Ile Lys Asp
    130                 135                 140

Leu Leu Ser Ser Asp Ser Phe Asn Ala Asp Thr Arg Leu Val Leu Val
145                 150                 155                 160
```

Asn Ala Leu Tyr Phe Lys Gly Asn Trp Lys Thr Gln Phe Asp Ala Met
            165                 170                 175

Asn Thr Ile Glu Gln Pro Phe His Ile Asp Ala Gln Thr Ser Val Asn
        180                 185                 190

Ile Pro Met Met Phe Gln Glu Glu Lys Phe Lys Tyr Gly Glu Ser Ser
            195                 200                 205

Asp Leu Gln Ala Gln Leu Leu Glu Met Lys Tyr Glu Gly Gly Asp Ala
        210                 215                 220

Ser Met Val Ile Val Leu Pro Asn Glu Ile Asp Gly Leu Asp Gly Val
225                 230                 235                 240

Met Gln Lys Leu Ala Asp Gly Tyr Asp Leu Met Ser Glu Val Glu Lys
            245                 250                 255

Met Phe Ser Thr Lys Val Lys Val Thr Leu Pro Lys Phe Lys Ile Glu
            260                 265                 270

Thr Glu Ile Asp Leu Met Glu Val Leu Pro Gln Leu Gly Ile Lys Ala
            275                 280                 285

Ile Phe Gly His Gly Asp Ser Gly Leu Ser Lys Ile Leu Asn Thr Gly
            290                 295                 300

Glu Pro Leu Tyr Val Ser Lys Ala Val Gln Lys Ala Tyr Ile Glu Val
305                 310                 315                 320

Asn Glu Glu Gly Ala Glu Ala Ala Ala Thr Gly Met Val Met Met
            325                 330                 335

Leu Arg Cys Ala Pro Met Pro Ser Pro His Phe Arg Ala Asp His Pro
            340                 345                 350

Phe Leu Tyr Leu Leu Val Gly Pro Asn Arg Ala Thr Leu Phe Ile Gly
            355                 360                 365

Val Phe Arg Ala Lys
        370

<210> SEQ ID NO 9
<211> LENGTH: 561
<212> TYPE: RNA
<213> ORGANISM: Spodoptera frugiperda

<400> SEQUENCE: 9
ccugcgcccc guggcgugcc ucagaucgag gucaccuucg acaucgaugc uaacgguauc      60
cuuaacguau cugccgucga gaagucuacc aacaaagaga acaagauuac cauuaccaac     120
gacaagggcc gucuuucaaa ggaggagauu gagcguaugg uuaacgaggc cgagaaguac     180
aggacugaag acgagaagca gaaggagacc auucaggcua agaaugccuu ggaaucuuac     240
uguuucgaca ugaaguccac cauggaggac gagaagcuca aggacaaaau cucagacucc     300
gacaagcaga caauccugga caagugcaac gacaccauca aauggcucga ucccaaccag     360
cuggcugaca aggaggaaua ugagcacaag caaaaagaac uggaagguau cugcaaucccc    420 aucauuacca agauguacca gggagcgggu gguaugccug gcgguaugcc cggaggcaug     480
ccuggauucc cugguggcgc acccggugcc ggaggcgcug ucccggugg cggugccgga      540 cccaccaucg aggaggucga c                                              561

<210> SEQ ID NO 10
<211> LENGTH: 408
<212> TYPE: RNA
<213> ORGANISM: Spodoptera frugiperda

<400> SEQUENCE: 10

-continued

```
gcugcccaga ccaaggccau gaagcaggug gcugguucca ugaagcugga guuggcccag      60
uaccgugagg ucgcugccuu cgcucaguuc gguccgacu uggacgccgc cacccagcaa      120
uugcugaacc gugguaugcg ucugacugag cugcugaagc agggacagua ugugcccaug     180
gccauugagg aacaggucgc caucaucuac uggugcc guggucaccu cgacaaacuu        240
gaccccagca agaucacugg cuucgagaag gaguuccaccc agcacaucaa gaccagccac    300
cagggucugc uggcuaccau cgccaaggac ggucagauca cccccgaguc ugacgccgcc    360
cucaagaaga ucgucacaga cuuccuagcu acuuucaccc aaucgcag                 408
```

<210> SEQ ID NO 11
<211> LENGTH: 428
<212> TYPE: RNA
<213> ORGANISM: Spodoptera frugiperda

<400> SEQUENCE: 11

```
ugucccgugc uauugcugag cuggguaucu accccgcugu ggaccccucc gacucuacuu     60
cccguaucau ggaccccaac auuauuggug cugagcacua caauguggcu cgugguguccc   120 agaagauccu ucaggacuac aagucacucc aggacaucau cgcuauccug gguauggaug    180
aguugucuga ggaagacaag cugacugucg cucgcgcccg uaagauccag agguucuugu    240
cccagccuuu ccagguugcu gagguguuca cuggacaugc uggcaaacug gugcccuug     300 aggagaccau caagggcuuc ucuaaaauce ugcagggcga guaugaucac cuaccugaag    360
uagcguucua caugguugga ccuauugagg agguugggc caaagcugau acucuugcua     420
agaaugcu                                                             428
```

EXPRESSION CASSETTE AND HOST CELL FOR EXPRESSING A VIP3-INTERACTING PROTEIN

CROSS REFERENCE TO RELATED APPLICATIONS

This application is a divisional of U.S. application Ser. No. 16/100,824, filed Aug. 10, 2018, now U.S. Pat. No. 10,836,801, which is a divisional of U.S. application Ser. No. 15/120,563, filed Aug. 22, 2016, now abandoned, which is the National Stage of International Application No. PCT/EP2015/054100, filed Feb. 26, 2015, which claims priority to U.S. Provisional Application No. 61/945,454, filed Feb. 27, 2014, all of which are incorporated herein by reference in their entirety.

REFERENCE TO A SEQUENCE LISTING

A Sequence Listing in ASCII text format, submitted under 37 C.F.R. § 1.821, entitled "73666-US-REG-D-NAT-2_SeqList_ST25.txt", 30 kilobytes in sin, generated on Sep. 30, 2020 and filed via EFS-Web, is provided in lieu of a paper copy. This Sequence Listing is hereby incorporated by reference into the specification for its disclosures.

FIELD OF THE INVENTION

The present invention relates generally to the field of molecular biology. More specifically, the field of the invention relates to polypeptides that interact with Vip3 toxin. The polypeptides are useful for developing new insecticidal agents.

BACKGROUND

Plant pests are a major factor in the loss of the world's important agricultural crops. About $8 billion are lost every year in the U.S. alone due to infestations of non-mammalian pests including insects. In addition to losses in field crops, insect pests are also a burden to vegetable and fruit growers, to producers of ornamental flowers, and to home gardeners.

Insect pests are mainly controlled by intensive applications of chemical pesticides, which are active through inhibition of insect growth, prevention of insect feeding or reproduction, or cause death. Good insect control can thus be reached, but these chemicals can sometimes also affect other, beneficial insects. Another problem resulting from the wide use of chemical pesticides is the appearance of resistant insect varieties. This has been partially alleviated by various resistance management practices, but there is an increasing need for alternative pest control agents. Biological pest control agents, such as *Bacillus thuringiensis* (Bt) strains expressing pesticidal toxins like δ-endotoxins, have also been applied to crop plants with satisfactory results, offering an alternative or complement to chemical pesticides. The genes coding for some of these δ-endotoxins have been isolated and their expression in heterologous hosts have been shown to provide another tool for the control of economically important insect pests. In particular, the expression of Bt δ-endotoxins has provided efficient protection against selected insect pests, and transgenic plants expressing such toxins have been commercialized, allowing farmers to reduce applications of chemical insect control agents.

Another family of insecticidal proteins produced by *Bacillus* species during the vegetative stage of growth (vegetative insecticidal proteins (Vip)) has also been identified. U.S. Pat. Nos. 5,877,012, 6,107,279, and 6,137,033, herein incorporated by reference, describe a class of insecticidal proteins called Vip3. Other disclosures, including WO 98/18932, WO 98/33991, WO 98/00546, and WO 99/57282, have also now identified homologues of the Vip3 class of proteins. Vip3 coding sequences encode approximately 88 kDa proteins that possess insecticidal activity against a wide spectrum of lepidopteran pests, including but not limited to black cutworm (BCW, *Agrotis ipsilon*), fall armyworm (FAW, *Spodoptera frugiperda*), tobacco budworm (TBW, *Heliothis virescens*), sugarcane borer, (SCB, *Diatraea saccharalis*), lesser cornstalk borer (LCB, *Elasmopalpus lignosellus*), and corn earworm (CEW, *Helicoverpa zea*). When expressed in transgenic plants, for example corn *Zea mays*), Vip3 coding sequences confer protection to the plant from insect feeding damage.

Vip3A is successful as an insecticidal protein in transgenic maize (U.S. Pat. Nos. 6,107,279, 8,232,456 herein incorporated by reference). The identification of proteins which interact with a Vip3 provides the ability to screen for other agents (e.g., proteins and/or chemicals) that may also have insecticidal properties. The present invention provides Vip3 interacting polypeptides and methods for screening for Vip3 interacting agents having cytotoxic and/or insecticidal properties.

SUMMARY OF THE INVENTION

The present invention is drawn to polypeptides that interact with Vip3 (e.g., from insect pests susceptible to Vip3 toxin) and methods of using those polypeptides to identify agents (e.g., ligands) that bind to Vip3 interacting polypeptides and/or modulate the activity of at least one Vip3 interacting polypeptide.

The invention includes polypeptides identified as interacting with Vip3. In representative embodiments, the invention provides recombinant Vip3 interacting polypeptides. In embodiments, the invention provides non-naturally occurring Vip3 interacting polypeptides. Optionally the Vip3 interacting polypeptide comprises, consists essentially of, or consists of the amino acid sequence of any of SEQ ID NOs: 1-8 or a substantially similar or substantially identical amino acid sequence thereto.

The invention also includes recombinant polynucleotide sequences which encode the above polypeptides, and vectors, expression cassettes and cells comprising the above mentioned polynucleotide sequences.

The invention includes a method for using Vip3-interacting polypeptides to identify other polypeptides that act in the same pathway, thereby elucidating mode of action; to identify agents that interact with (e.g., bind) Vip3-interacting polypeptides, to identify agents that have insecticidal properties; to identify polypeptides that bind to Vip3, and to elucidate the mode of action of a different Vip3 in a different insect system.

Also provided by the invention is a method of identifying an agent that interacts with at least one Vip3 interacting polypeptide. The agent may interact with a single Vip3 interacting polypeptide, with multiple Vip3 interacting polypeptides individually, or with a complex of Vip3 interacting polypeptides which may include other polypeptides (that do or do not interact with Vip3). In a representative embodiment, the method of identifying the agent comprises contacting at least one Vip3 interacting polypeptide or fragment thereof (optionally, a biologically active fragment), acting individually or as part of a complex, to one or more test agents, and then detecting binding activity between the Vip3 interacting polypeptide(s) under conditions sufficient for binding. Binding activity can be measured by any method known in the art, e.g., by measuring desired binding characteristics, including but not limited to binding affinity, binding site specificity, and/or association and dissociation rates. Binding activity can also be determined qualitatively, such as in a gel-shift assay. In representative embodiments, binding between the Vip3 interacting polypeptide(s) and the test agent indicates that the test agent is a candidate insecticidal agent.

In another embodiment of the invention, the method further comprises measuring the cytotoxicity and/or insecticidal activity of the candidate insecticidal agent (e.g., in a cell based or live insect based system).

Also provided by the invention is a method of identifying an agent that modulates the activity of at least one Vip3 interacting polypeptide. In representative embodiments, the method comprises contacting at least one Vip3 interacting polypeptide or a fragment thereof (optionally, a biologically active fragment) with a test agent in a cell (e.g., an insect cell), for example, from a heterologous nucleotide sequence(s), and detecting cytotoxicity under conditions sufficient to provide cytotoxicity. A change in the level of cytotoxicity compared to the level of cytotoxicity in the absence of the test agent indicates that the test agent is an agent that modulates the activity of at least one Vip3 interacting polypeptide.

Optionally, in fixe methods of the invention, the agent is a *Bacillus* polypeptide(s).

Also provided by the invention is a method of identifying an insecticidal and/or cytotoxic agent that interacts with at least one Vip3 interacting polypeptide or a fragment (e.g., a biologically active fragment) thereof. In representative embodiments, the method comprises contacting at least one Vip3 interacting polypeptide or fragment thereof to a *Bacillus* polypeptide(s); isolating a Vip3 interacting polypeptide under conditions appropriate for co-purification with a ligand, identifying a co-purified polypeptide, and determining the insecticidal and/or cytotoxic activity of the co-purified polypeptide.

Further provided is a method of identifying a cytotoxic agent that interacts with at least one Vip3 interacting polypeptide, said method comprising: a. providing at least one Vip3 interacting polypeptide or fragment thereof (e.g., a biologically active fragment) expressed in a cell (optionally an insect cell), wherein the cell is not susceptible to Vip3 toxin; b. contacting the at least one Vip3 interacting polypeptide or fragment with a test agent under conditions sufficient to promote binding, and detecting cytotoxicity of the cell, wherein an increase in the level cytotoxicity as compared with the level of cytotoxicity in the absence of the test agent indicates that the test agent is a cytotoxic agent. In embodiments, the cytotoxicity of the combination of the Vip3 interacting polypeptide and the test agent is greater (e.g., at least 25%, 50%, 75%, 100%, 200% or more greater) than the cytotoxicity of either alone. In representative embodiments, neither the Vip3 interacting polypeptide nor the test agent shows significant cytotoxicity on its own.

In another embodiment of the invention, test agents can comprise environmental samples, biological samples, chemical libraries, or cellular extracts.

A further embodiment is a ligand of a Vip3 interacting polypeptide identified by a method of the invention.

Another embodiment is a candidate insecticidal agent identified by a method of the invention.

BRIEF DESCRIPTION OF THE SEQUENCES

SEQ ID NO 1: depicts the polypeptide sequence of ATP synthase α from *S. frugiperda.*

SEQ ID NO 2: depicts the polypeptide sequence of ATP synthase β from *S. frugiperda*

SEQ ID NO 3: depicts the polypeptide sequence of Hsc70 from *S. frugiperda*

SEQ NO 4: depicts the polypeptide sequence of prohibitin-1 from *H. zea.*

SEQ ID NO 5: depicts the polypeptide sequence of prohibitin-1 from *M. sexta*

SEQ ID NO 6: depicts the polypeptide sequence of prohibitin-2 from *H. zea*

SEQ ID NO 7: depicts the polypeptide sequence of prohibitin-2 from *M. sexta.*

SEQ ID NO 8: depicts the polypeptide sequence of serpin from *H. sexta.*

SEQ ID NO 9: depicts one strand of the double-stranded RNA of Hsc70 from *S. frugiperda* used for dsRNA experiments in examples 12 and 13.

SEQ NO 10: depicts one strand of the double-stranded RNA of ATP synthase α from *S. frugiperda* used for dsRNA experiments in examples 12 and 13.

SEQ ID NO 11: depicts one strand of the double-stranded RNA of ATP synthase β from *S. frugiperda* used for dsRNA experiments in examples 12 and 13.

DETAILED DESCRIPTION OF THE INVENTION

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety As used herein, "a," "an" or "the" can mean one or more than one. For example, a cell can mean a single cell or a multiplicity of cells.

As used herein, "and/or" refers to and encompasses any and all possible combinations of one or more of the associated listed items, as well as the lack of combinations when interpreted in the alternative (or).

Further, the term "about," as used herein when referring to a measurable value such as an amount of a compound or agent, dose, time, temperature, and the like, is meant to encompass variations of =20%, ±10%, +5%, ±1%, +0.5%, or even ±0.1% of the specified amount.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

It will be understood that, although the terms "first," "second," etc. may be used herein to describe various elements, these elements should not be limited by these terms. These terms are only used to distinguish one element from another. Thus, a "first" element (e.g., a first promoter sequence) as described herein could also be termed a "second" element (e.g., a second promoter sequence) without departing from the teachings of the present invention.

For purposes of the present invention, "insect" or "insect pest" include without limitation insects and arachnids selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, and Acari, particularly Coleoptera and Lepidoptera. In particular, insect pests include black cutworm (*Agrotis ipsilon*), fall armyworm (*Spodoptera frugiperda*), beet armyworm (*S. exigua*), yellow striped armyworm (*S. ornithogalli*), southwestern corn borer (*Diatraea grandiosella*), sugarcane borer (*D. saccharalis*), corn earworm (*Helicoverpa zea*), Mediterranean corn borer (*Sesamia nonagroides*), cabbage looper (*Trichoplusia ni*), velvetbean caterpillar (*Anticarsia gemmatalis*), diamondback moth (*Plutella xylostella*), tobacco budworm (*Heliothis virescens*), European corn borer (*Ostrinia nubilalis*), western corn rootworm (*Diabrotica virgifera virgifera*), southern corn rootworm (*Diabrotica undecimpunctata howardi*), northern corn rootworm (*Diabrotica barberi*).

The term "Vip3" as used herein is intended broadly and encompasses naturally occurring Vip3 polypeptides including but is not limited to Vip3A (e.g., Vip3A(a), Vip3A(b), Vip3A(c)), Vip3B, Vip3C, Vip3D, Vip3E) and any other protein now known or later identified as a Vip3 (see. e.g., the database of Vip3 toxin nomenclature found on the worldwide web at lifesci.sussex.ac.uk/home/Neil_Crickmore/Bt/vip.html) and equivalents of any of the foregoing (including engineered Vip3 polypeptides and Vip3 fragments). The term Vip3 also includes polypeptides that are substantially similar or substantially identical at the amino acid level to the toxic core region of a Vip3 protein, optionally while also substantially retaining at least one Vip3 biological activity (e.g., insecticidal and/or cytotoxic activity). The term "Vip3" further includes modifications (e.g., deletions and/or truncations) of a naturally occurring Vip3 or an equivalent thereof that has a substantially similar or substantially identical amino acid sequence to a naturally occurring Vip3. Exemplary Vip3 equivalents have been disclosed in 8118932, WO 98/3399_, WO 98/00546, and WO 99/57282.

Further, the Vip3 can be from any bacterial genus or species of origin including without limitation a *Bacillus* species e.g., *B. cerues*, *B. thuringiensis*, and the like), *Clostridium*, or other soil-borne bacteria.

In embodiments, a Vip3 equivalent comprises a fragment of a naturally-occurring or non-naturally occurring full-length Vip3 polypeptide, optionally a biologically active fragment.

In representative embodiments, a biologically active equivalent of a Vip3 polypeptide, a biologically active fragment of a Vip3 polypeptide, or a biologically active equivalent thereof, comprises the toxic core region of a naturally-occurring Vip3 protein, or an amino acid sequence that is substantially similar or substantially identical to the toxic core region of a naturally-occurring Vip3 protein.

A polypeptide that is "substantially similar" or "substantially identical" to a reference amino acid sequence is 1) a polypeptide that is at least about 70%, 75%, 80%, 85%, 90%, 95%, 96%, 97%, 98%, 99%, or more than 99% similar or identical at the amino acid sequence level to the referenced polypeptide, optionally while also substantially retaining at least one activity associated with the reference polypeptide, 2) a polypeptide that is cross-reactive to an antibody that immunologically recognizes the reference polypeptide, and/or 3) a polypeptide that is cross-reactive with a receptor bound by the referenced polypeptide and, optionally, acts as a receptor agonist.

The proteins of the Vip3 class are secreted into the media by *Bacillus* spp, in vegetative stages of growth. For example, the Vip3: protein (e.g., Vip3A(a) protein) is a member of a distinct class of proteins displaying insecticidal activity against a broad spectrum of lepidopteran insects including black cutworm (*Agrotis ipsilon*), fall armyworm (*Spodoptera frugiperda*), tobacco hornworm (*Manduca sexta*), beet armyworm (*S. exigua*), yellow striped armyworm (*S. ornithogalli*), southwestern corn borer (*Diatraea grandiosella*), sugarcane borer (*D. saccharalis*), corn earworm (*Helicoverpa zea*), Mediterranean corn borer (*Sesamia nonagroides*), cabbage looper (*Trichoplusia ni*), velvetbean caterpillar (*Anticarsia gemmatalis*), diamondback moth (*Plutella xylostella*) and tobacco budworm (*Heliothis virescens*).

As discussed above, Vip3A protein (e.g., Vip3A(a) protein) has been shown to be active against a broad spectrum of plant pests. For example, histopathological observations indicate that Vip3A ingestion by susceptible insects such as black cutworm (*Agrotis epsilon*) and fall armyworm (*Spodoptera frugiperda*) causes gut paralysis at concentrations as low as 4 ng/cm$^2$ of diet, with complete lysis of the gut epithelial cells resulting in larval death at concentrations above 40 ng/cm$^2$. Less susceptible insects like European corn borer (*Ostrinia nubilalis*) do not develop any pathology upon ingesting Vip3A. While the proteolytic processing of the Vip3A protein by midgut fluids obtained from susceptible and non-susceptible insects is comparable, in vivo immuno-localization studies show that Vip3A(a) binding is restricted to gut cells of susceptible insects. Therefore, the insect host range for Vip3A seems to be determined by its binding ability to gut cells. Histopathological observations indicate that midgut epithelial cells of susceptible insects are the primary target for the Vip3A insecticidal protein and their subsequent lysis is the primary mechanism of lethality.

Immunohistochemistry indicates that Vip3A (e.g., Vip3A (a)) has the ability to bind to the apical membranes of midgut epithelial cells and that this binding triggers the process that will eventually end with cell lysis. This indicates that there exists one or more proteins located in the apical membrane that recognize and bind to Vip3A.

As used herein, the "activity" or "biological activity" of a Vip3 protein includes any biological activity of a Vip3 protein including without limitation insecticidal activity, cytotoxic activity and/or binding activity.

"Insecticidal activity" refers to activity as an insect control agent (e.g., an orally active insect control agent), for example, by inhibiting, through a toxic effect, the ability of one or more insect species to survive, grow, feed, and/or reproduce, which may or may not cause death of the insect.

As used herein, to "control insects" (and similar terms) means to inhibit, through a toxic effect, the ability of an insect pest to survive, grow, feed, and/or reproduce, and/or to limit insect-related damage and/or loss in crop plants. The term "control insects" may or may not mean killing the insects, although in representative embodiments, one or more insect pests are killed.

As used herein, "toxicity" refers to the decreased viability of a cell, and "viability" refers to the ability of a cell to proliferate and/or differentiate and/or maintain its biological characteristics in a manner characteristic of that cell in the absence of a particular cytotoxic agent.

"Expression cassette" as used herein means a nucleic acid (e.g., DNA) sequence capable of directing expression of a gene in a cell (e.g., a plant, insect, or bacterial cell), comprising a promoter operably linked to an amino acid coding region which is operably linked to a termination region. The gene may be chimeric, meaning that at least one component of the gene is heterologous with respect to at least one other component of the gene. The gene may also be naturally occurring, but which has been obtained in a recombinant form useful for genetic transformation of a plant or microorganism.

As used herein, the term "nucleic acid," "nucleic acid molecule," "polynucleotide" and/or "nucleotide sequence" refers to a heteropolymer of nucleotides or the sequence of these nucleotides from the 5' to 3' end of a nucleic acid molecule and includes DNA or RNA molecules, including cDNA, a DNA fragment, genomic DNA, synthetic (e.g., chemically, synthesized) DNA, plasmid DNA, mRNA, and anti-sense RNA, any of which can be single stranded or double stranded or a combination of both. The terms "nucleotide sequence" "nucleic acid," "nucleic acid molecule," "oligonucleotide" and "polynucleotide" are also used interchangeably herein to refer to a heteropolymer of nucleotides. Nucleic acid sequences provided herein are presented herein in the 5' to 3' direction, from left to right and are represented using the standard code for representing the nucleotide characters as set forth in the sequence rules for the U.S. Patent and Trademark Office, 37 CFR §§ 1.821-1.825, and the World Intellectual Property Organization (WIPO) Standard ST.25.

In embodiments, nucleic acids according to the present invention are non-naturally occurring nucleic acids. In embodiments, nucleic acids according to the present invention are recombinant nucleic acids.

As used herein, the term "gene" is used broadly to refer to any segment of nucleic acid associated with a biological function. Thus, genes include coding sequences and/or the regulatory sequences required for their expression. For example, "gene" refers to a nucleic acid fragment that expresses mRNA or functional RNA, or encodes a specific protein, and which includes regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

The terms "complementary" or "complementarity," as used herein, refer to the natural binding of polynucleotides under permissive salt and temperature conditions by base-pairing. For example, the sequence "A-G-T" binds to the complementary sequence "T-C-A." Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

An "isolated" nucleic acid or polynucleotide of the present invention is generally free of nucleic acid sequences that flank the nucleic acid of interest in the genomic DNA of the organism from which the nucleic acid was derived (such as coding sequences present at the 5' or 3' ends). However, the nucleic acid of this invention can include some additional bases or moieties that do not deleteriously affect the basic structural and/or functional characteristics of the nucleic acid. An "isolated" nucleic acid or polynucleotide includes a chimeric molecule or a cDNA which may not be naturally occurring. "Isolated" does not necessarily mean that the preparation is technically pure (homogeneous).

Thus, an "isolated nucleic acid" or "isolated polynucleotide" is present in a form or setting that is different from that in which it is found in nature and is not immediately contiguous with nucleotide sequences with which it is immediately contiguous (one on the 5' end and one on the 3' end) in the naturally occurring genome of the organism from which it is derived. Accordingly, in one embodiment, an isolated nucleic acid includes some or all of the 5' non-coding (e.g., promoter) sequences that are immediately contiguous to a coding sequence. The term therefore includes, for example, a recombinant nucleic acid that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. Thus, a nucleic acid found in nature that is removed from its native environment and transformed into a plant is still considered "isolated" even when incorporated into the genome of the resulting transgenic plant. It also includes a recombinant nucleic acid that is part of a hybrid nucleic acid encoding an additional polypeptide or peptide sequence.

The term "isolated" can further refer to a nucleic acid, nucleotide sequence, polypeptide, peptide or fragment that is substantially free of cellular material, viral material, and/or culture medium (e.g., when produced by recombinant DNA techniques), or chemical precursors or other chemicals (e.g., when chemically synthesized). Moreover, an "isolated fragment" is a fragment of a nucleic acid, nucleotide sequence or polypeptide that is not naturally occurring as a fragment and would not be found as such in the natural state. "Isolated" does not mean that the preparation is technically pure (homogeneous), hut it is sufficiently pure to provide the polypeptide or nucleic acid in a form in which it can be used for the intended purpose.

The terms "polypeptide," "protein," and "peptide" refer to a chain of covalently linked amino acids. In general, the term "peptide" can refer to shorter chains of amino acids (e.g., 2-50 amino acids); however, all three terms overlap with respect to the length of the amino acid chain. As used herein, the terms "protein" and "polypeptide" are used interchangeably and encompass peptides, unless indicated otherwise. Polypeptides, proteins, and peptides may comprise naturally occurring amino acids, non-naturally occurring amino acids, or a combination of both. The polypeptides, proteins, and peptides may be isolated from sources (e.g., cells or tissues) which they naturally occur, produced recombinantly in cells in vivo or in vitro or in a test tube in vitro, or synthesized chemically. Such techniques are known to those skilled in the art. See, e.g., Sambrook et al., Molecular Cloning: A Laboratory Manual 2nd Ed. (Cold Spring Harbor, N.Y., 1989); Ausubel et al. Current Protocols in Molecular Biology (Green Publishing Associates, Inc. and John Wiley & Sons, Inc., New York).

In embodiments, the polypeptides and polynucleotides of the invention can be recombinant (produced by genetic engineering), and can optionally be chimeric. In representative embodiments, polypeptides according to the present invention are non-naturally occurring polypeptides.

The term "fragment," as applied to a polypeptide, will be understood to mean an amino acid sequence of reduced length relative to a reference polypeptide or amino acid sequence and comprising, consisting essentially of, and/or consisting of an amino acid sequence of contiguous amino acids identical to the reference polypeptide or amino acid sequence. Such a polypeptide fragment according to the invention may be, where appropriate, included in a larger polypeptide of which it is a constituent (e.g., a fusion protein). In some embodiments, such fragments can comprise, consist essentially of, and/or consist of peptides having a length of at least about 4, 6, 8, 10, 12, 15, 20, 25, 30, 35, 40, 45, 50, 75, 100, 150, 200, or more consecutive amino acids of a polypeptide or amino acid sequence according to the invention. A fragment of a polypeptide or protein can be produced by methods well known and routine in the art, for example, by enzymatic or other cleavage of naturally occurring peptides or polypeptides or by synthetic protocols that are well known.

A polypeptide fragment can optionally be a biologically active fragment. A "biologically active fragment" or "active fragment" refers to a fragment that substantially retains (e.g., at least about 25%, 30% 35%, 40%, 45%, 50%, 55%, 60%, 65%, 70%, 75%, 80%, 85%, 90%, 95% or more) one or more of the biological activities of the reference polypeptide. Such fragments can be tested for biological activities according to methods described in the art. For example, an active fragment of a Vip3 protein can be tested for binding to a Vip3 interacting polypeptide, insecticidal activity, and/ or cytotoxic activity. Thus, the present invention further provides biologically active fragments of a polypeptide and the polynucleotides encoding such biologically active polypeptide fragments.

The term "agent" as used herein refers to a molecule that is a candidate binding partner e.g., ligand) for a Vip3 interacting polypeptide and/or candidate toxin identified by its cytotoxic effect in the presence of a Vip3 interacting polypeptide. The term "ligand" as used herein refers to a substance that can specifically bind with a biomolecule, such as a Vip3 interacting polypeptide. Optionally, the agent can modulate the activity (e.g., an antagonist or an agonist) of its binding partner (e.g., Vip3 interacting polypeptide) and/or a downstream pathway. In representative embodiments, the "agent" is a polypeptide (including modified polypeptides such as glycoproteins), a carbohydrate (including a sugar), a lipid, a nucleic acid (including nucleic acids comprising modified bases or a small molecule. In representative embodiments, the test agent comprises a protein extract or polypeptide from one or more *Bacillus* spp. Candidate agents further include molecules available from diverse libraries of small molecules created by combinatorial synthetic methods. Candidate agents also include, but are not limited to antibodies, peptides, aptamers, and other small molecules designed or deduced to interact with the Vip3 interacting polypeptides of the invention. Agents identified by the screening methods of the invention include potential novel insecticidal toxins, the insecticidal activity of which can be determined by known methods, such as feeding assays as described in U.S. Pat. Nos. 5,407,454; 6,232,439; and Marrone et al (1985) J. of Economic Entomology 78:290-293 (each herein incorporated by reference).

As used herein, the term "modulate" or "modulates" (and similar terms) indicates an increase or decrease in the referenced activity of at least about 10%, 15%, 20%, 25%, 30%, 40%, 50%, 60%, 75%, 100%, 200%, or more.

An "environmental sample" is a sample of any material that is collected from an environmental source, including but not limited to water samples such as that from ponds, lakes, or rivers; soil samples; samples of air-borne particles; samples of vegetation; or smear samples from surfaces.

A "biological sample" is a sample of any material that is collected from a biological source, including but not limited to tissue samples from any part of any plant, insect, or animal, including blood, serum, or cell culture; or microorganism cultures, including but not limited to such microorganisms as fungi, yeast, bacteria, or algae.

A "chemical library" is a series of stored chemicals. Each chemical has associated information stored in some kind of database with information including but not limited to the chemical structure, purity, quantity, and/or physiochemical characteristics of the compound. Chemical libraries include molecules available from diverse libraries of small molecules created by combinatorial synthetic methods.

The present invention is based, in part, on the identification of Vip3 interacting polypeptides from insects susceptible to Vip3 toxin based on their interaction with Vip3. A "Vip3 interacting polypeptide" is a polypeptide that interacts (e.g., binds covalently and/or non-covalently) with Vip3, for example, in a binding assay. In embodiments, the Vip3 interacting polypeptide is from an insect susceptible to Vip3 toxin, although it may be produced in recombinant form rather than being isolated from its native source. In embodiments, the Vip3 interacting polypeptide binds directly to Vip3. In embodiments, the Vip3 interacting polypeptide binds indirectly to Vip3 (e.g., as part of a complex, another component of which binds directly to Vip3). In embodiments, the Vip3 interacting polypeptide of the invention is ATP synthase α, ATP synthase β, Hsc-70, prohibitin-1, prohibitin-2, and/or serpin. These polypeptides may interact with Vip3 individually, with each other, and/or with other proteins (e.g., insect proteins), and may optionally participate in the mod of action of Vip3. Combinations comprising Vip3 and ATP synthase α, ATP synthase β, prohibitin-1, prohibitin-2, serpin, and/or other proteins (e.g., insect proteins) that result in insecticidal activity and/or cytotoxicity of insect cells (e.g., insect cells susceptible to Vip3 toxin) are also encompassed in the present invention.

In representative embodiments, the Vip3 interacting agent is provided as part of a cellular extract.

In representative embodiments, the agent interacting with Vip3 interacting polypeptide is provided is provided as part of a cellular extract.

In representative embodiments, the Vip3 interacting polypeptide of the invention binds to a Vip3 and/or mediates cytotoxic activity in the presence of Vip3.

In representative embodiments, the Vip3 interacting polypeptide comprises, consists essentially of, or consists of prohibitin-1 and prohibitin-2.

In representative embodiments, the Vip3 interacting polypeptide comprises, consists essentially of, or consists of ATP synthase α and ATP synthase β.

The terms "ATP synthase α", "ATP synthase β", "Hsc-70", "prohibitin-1", "prohibitin-2", and "serpin" are intended broadly herein and encompass naturally occurring polypeptides now known or later identified and equivalents of any of the foregoing (including engineered polypeptides and fragments) that retain at least one biological activity of the native protein (e.g., binds Vip3 and/or forms a complex that binds Vip3). These terms further include modifications (e.g., deletions and/or truncations) of a naturally occurring polypeptide or an equivalent thereof that has a substantially similar or substantially identical amino acid sequence to a naturally occurring polypeptide and that retains at least one biological activity associated with the naturally occurring polypeptide. Further, the ATP synthase α, ATP synthase β, Hsc-70, prohibitin-1, prohibitin-2, or serpin polypeptide can be from any species of origin including without limitation an insect species (for example, from a lepidopteran insect species, from a coleopteran insect species, from the genus *Spodoptera* [e.g., *S. frugiperda*], the genus *Helicoverpa* [e.g., *H. zea*], the genus *Manduca* [e.g., *M. sexta*]), the genus *Ostrinia* (e.g. *O. nubilalis*) or the genus *Diabrotica* (e.g. *D. virgifera*). Those skilled in the art will appreciate that the specific Vip3 interacting polypeptides and nucleic acids encoding the same disclosed herein can be used to identify corresponding Vip3 interacting polypeptides in other species (e.g., insect species, optionally a Vip3 susceptible insect species).

In embodiments, an ATP synthase α, ATP synthase β, Hsc-70, prohibitin-1, prohibitin-2, or serpin equivalent comprises a fragment of a naturally-occurring or non-naturally occurring full-length polypeptide, optionally a biologically active fragment (e.g., substantially retains the ability to interact with Vip3, to bind Vip3, to form a complex that interacts with or binds Vip3, enzymatic activity and/or protease inhibition activity).

In representative embodiments, a biologically active equivalent of an ATP synthase α, ATP synthase β, Hsc-70, prohibitin-1, prohibitin-2, or serpin polypeptide or a biologically active fragment thereof is a soluble fragment that comprises a Vip3 binding domain, or an amino acid sequence that is substantially similar or substantially identical to the Vip3 binding domain of a naturally-occurring ATP synthase α, ATP synthase β, Hsc-70, prohibitin-1, prohibitin-2, and/or serpin.

In representative embodiments, the Vip3 interacting polypeptide comprises, consists essentially of, or consists of ATP synthase α from *Spodoptera frugiperda*, ATP synthase β from *S. frugiperda*, Hsc70 from *S. frugiperda*, prohibitin-1 from *Helicoverpa zea* and/or from *Manduca* sexta, prohibitin-2 from *H. zea* and/or from *M. sexta*, or serpin from *Manduca sexta*, and any combination of the foregoing.

In representative embodiments, the Vip3 interacting polypeptide comprises, consists essentially of, or consists of the amino acid sequence of any of SEQ ID NOS: 1-8 or equivalents thereof (including fragments and equivalents thereof). Equivalents of the Vip3 interacting polypeptides encompass those that have substantial amino acid sequence identity or similarity with any of SEQ ID NOS: 1-8 or a fragment thereof, optionally a biologically active fragment.

It will be understood that naturally occurring polypeptides will typically tolerate substitutions in the amino acid sequence and substantially retain biological activity. To routinely identify biologically active polypeptides other than naturally occurring Vip3 or the Vip3 interacting polypeptides of SEQ ID NOs: 1-8), amino acid substitutions may be based on any characteristic known in the art, including the relative similarity or differences of the amino acid side-chain substituents, for example, their hydrophobicity, hydrophilicity, charge, size, and the like. In particular embodiments, conservative substitutions (i.e., substitution with an amino acid residue having similar properties) are made in the amino acid sequence encoding the Vip3 polypeptide or the Vip3 interacting polypeptide.

The invention further provides polynucleotides encoding the Vip3 interacting proteins of the invention, and vectors, expression cassettes and host cells comprising the same.

The compositions of the present invention are useful for, among other uses, expressing the Vip3 interacting polypeptides in cells to produce cellular or isolated preparations of the polypeptides for investigating the structure-function relationships of the Vip3 interacting polypeptides; investigating their interactions with Vip3 toxin; elucidating the mode of action n of Vip3 toxins; screening and identifying agents as ligands of Vip3 interacting polypeptides including insecticidal or cytotoxic toxins; and designing and developing ligands of Vip3 interacting polypeptides including insecticidal toxins.

Screening for ligands of Vip3 interacting polypeptides can be performed in a number of ways. For example, at least one recombinant or isolated nucleotide sequence encoding a Vip3 interacting polypeptide of the invention can be expressed in a cell of interest, and utilized in intact cell or in-vitro receptor binding assays, and/or intact cell toxicity assays. Methods and conditions for insect toxin binding and toxicity assays are known in the art and include but are not limited to those described in U.S. Pat. No. 5,693,491; Keeton et al. (1998) Appl. Environ. Microbiol. 64(6):2158-2165; Francis et al. (1997) Insect Biochem. Mol. Bio. 27(6):541-550; Keeton et al, (1997) Appl. Environ. Microbiol. 63(9):3419-3425; Vadlamudi et al. (1995) J. Biol. Chem. 270(10):5490-5494; Ihara et al. (1998) Comparative Biochem. Physiol. B25 120:197-204; and Nagamatsu et al. (1998) Biosci. Biotechnol, each herein incorporated by reference.

The term "cell of interest" as used herein refers to any cell in which expression of the polypeptides of the invention is desired. Cells of interest include, but are not limited to mammalian, avian, insect, plant, bacteria, fungi and yeast cells. Cells of interest further include but are not limited to cultured cell lines, primary cell cultures, cells in vivo, and cells of transgenic organisms.

The methods of the invention encompass using the polypeptides encoded by the nucleotide sequences of the invention in binding and/or toxicity assays to identify agents (e.g., ligands) that interact with a Vip3 toxin interacting polypeptide, including agents that are agonists or antagonists.

Agents may act by modulating the activity of a Vip3 interacting polypeptide, which, for example, may change the level of cytotoxicity as compared to the level of cytotoxicity in the absence of the agent. Modulating the activity may result in either an increase or decrease of cytotoxicity compared to the absence of the agent.

The invention provides methods for screening agents (e.g., ligands) that bind directly or indirectly to the Vip3 interacting polypeptides described herein. Both the Vip3 interacting polypeptides and fragments thereof (for example, the Vip3 toxin binding domain) can be used to screen for compounds that bind to at least one of the Vip3 interacting polypeptides and fragments thereof and optionally exhibit desired binding characteristics. Desired binding characteristics include but are not limited to binding affinity, binding site specificity, association and dissociation rates, and the like. The screening assay can be an intact cell or in vitro assay that includes exposing a Vip3 toxin binding domain to a sample ligand or agent and detecting the formation of a ligand-binding polypeptide complex. The assay can be a direct ligand-polypeptide binding assay or a ligand competition assay.

In representative embodiments, the Vip3 interacting polypeptide is a fusion protein comprising a detectable moiety (e.g., a poly-histidine sequence, a FLAG epitope, glutathione-S-transferase, maltose-binding protein, or a reporter protein [for example, Green Fluorescent Protein, ß-glucuronidase, ß-galactosidase, luciferase, etc.], hemagglutinin, c-myc, and the like.

For in vitro binding assays, the Vip3 interacting polypeptide(s) may be provided as isolated, lysed cellular extracts, or homogenized cellular preparations or a recombinant polypeptide. The polypeptides may be provided in solution, or immobilized to a matrix. Methods for immobilizing polypeptides are well known in the art, and include but are not limited to construction and use of fusion polypeptides with commercially available high affinity ligands. For example, GST fusion proteins can be adsorbed onto glutathione sepharose beads (Sigma Chemical, St. Louis, Mo.) or glutathione derivatized microtiter plates. The polypeptides can also be immobilized utilizing techniques in the art, such as using the conjugation of biotin and streptavidin. The polypeptides can also be immobilized utilizing techniques in the art utilizing chemical conjugation (linking) of polypeptides to a matrix. Alternatively, the polypeptides may be provided in intact cell binding assays in which the polypeptides are generally expressed from recombinant nucleic acids and the interaction is detected in situ using techniques in the art, such as FRET (see for example Masi et al. (2010) Adv. Exp. Ailed. Biol. 674: 33-42 and references cited within).

The present invention may utilize intact cell toxicity assays to screen for agents that hind to the Vip3 interacting polypeptides described herein and confer toxicity upon a cell of interest expressing the polypeptide. An agent selected by this screening method is a candidate a insecticidal agent (e.g., for an insect expressing the Vip3 interacting polypeptide), particularly enterally. Toxicity assays include without limitation exposing, in intact cells expressing a polypeptide of the invention, the toxin binding domain of the polypeptide to a sample agent and detecting the toxicity effected in the cell expressing the polypeptide.

In one embodiment, the methods of the present invention comprise providing at least Vip3 interacting polypeptide of the invention, contacting the polypeptide with a test agent under conditions promoting binding, and determining the viability of the cell expressing the cell surface Vip3 toxin interacting polypeptide. As used herein, "contacting" (and similar terms) means that the test agents are presented to the intended ligand binding site of the polypeptides of the invention. "Conditions promoting binding" (and similar terms) refers to any combination of physical and biochemical conditions that enables a ligand of the polypeptides of the invention to determinably bind the intended polypeptide over background levels. Examples of such conditions for binding of ligands to insect toxin receptors, as well as methods for assessing the binding, are known in the art and include but not limited to those described in Keeton et al. (1998) Appl Environ Microbiol 64(6): 2158-2165; Francis et al. (1997) Insect Biochem Mol Biol 27(6):541-550; Keeton et al. (1997) Appl Environ Microbiol 63(9):3419-3425; Vadlamudi et al. (1995) J Biol Chem 270(10):5490-5494; Ihara et al. (1998) Comparative Biochemistry and Physiology, Part B 120:197-204; and Nagamatsu et al. (1998) Biosci. Biotechnol. Biochem. 62(4):727-734, the contents of each which are herein incorporated by reference.

In carrying out the present invention, commercially available methods for studying protein-protein interactions, such as yeast and/or bacterial two-hybrid systems can also be used. Two-hybrid systems are available from, for example, CLONTECH (Palo Alto, Calif.).

The compositions and screening methods of the invention are useful for designing and developing ligands of Vip3 interacting polypeptides including insecticidal toxins. Candidate agents screened and characterized for binding, toxicity, and/or species specificity and/or ligands having known characteristics and specificities can be linked and/or modified to produce ligands having particularly desired characteristics and specificities. The methods described herein for assessing binding, toxicity and insecticidal activity can be used to screen and characterize the ligands.

A variety of sources can be used for screening for other agents that interact with the identified Vip3 interacting proteins. This includes but is not limited to biological samples, environmental samples, cellular extracts, or extracts from microorganisms such as *Bacillus* species. The cellular extracts tested in the methods of the present invention can be, as examples, aqueous extracts of cells or tissues, organic extracts of cells or tissues or partially purified cellular fractions. Extracts may comprise intracellular proteins, extracellular proteins, total cell extracts, or at least partially purified subcellular fractions. A skilled artisan can readily recognize that there is no limit as to the source of the cellular extract used in the screening method of the present invention.

Another embodiment of the present invention provides methods for identifying agents that bind to a Vip3 interacting polypeptide. In an exemplary embodiment, agents that bind to a Vip3 interacting polypeptide can be identified by: 1) the ability of the agent to bind at least one Vip3 interacting polypeptide, 2) the ability to block Vip3 binding to a Vip3 interacting polypeptide, and/or 3) the ability to kill cells expressing a Vip3 interacting polypeptide.

More particularly, in one embodiment, at least one Vip3 interacting polypeptide is mixed with an agent (e.g., a cellular extract or isolated molecule(s)). After mixing under conditions that allow association of the Vip3 interacting polypeptide(s) with the agent, the mixture is analyzed to determine if the agent binds to the Vip3 interacting polypeptide(s).

As another alternative, targets that are bound by a Vip3 interacting polypeptide can be identified using a yeast two-hybrid system or using a binding-capture assay. In the yeast two hybrid system, an expression unit encoding a fusion protein made up of one subunit of a two subunit transcription factor and the Vip3 interacting polypeptide is introduced and expressed in a yeast cell. The cell is further modified to contain 1) an expression unit encoding a detectable marker whose expression requires the two subunit transcription factor for expression and 2) an expression unit that encodes a fusion protein made up of the second subunit of the transcription factor and a cloned segment of DNA. If the cloned segment of DNA encodes a protein that binds to the Vip3 interacting polypeptide, the expression results in the interaction of the Vip3 interacting polypeptide and the encoded protein. This brings the two subunits of the transcription factor into binding proximity, allowing reconstitution of the transcription factor. This results in the expression of the detectable marker. The yeast two hybrid system is particularly useful in screening a library of cDNA encoding segments for cellular binding partners of the Vip3 interacting polypeptide.

The Vip3 interacting polypeptide used in the above assays can be a recombinant or isolated polypeptide, a fragment of a Vip3 interacting polypeptide (such as a soluble fragment containing the Vip3 binding site), a cell that has been altered to express a Vip3 interacting polypeptide or fragment or a fraction of a cell that has been altered to express a Vip3 interacting polypeptide or fragment. Further, the Vip3 interacting polypeptide can be the entire protein or a fragment thereof (e.g., a biologically active fragment) of the protein. It will be apparent to one of ordinary skill in the art that so long as the Vip3 interacting polypeptide or fragment can be assayed for ligand binding, e.g., by a shift in molecular weight or activity, the present assay can be used.

The method used to identify whether an agent binds to a Vip3 interacting polypeptide can be based on the nature of the Vip3 interacting polypeptide used. For example, a gel retardation assay can be used to determine whether an agent binds to a Vip3 interacting polypeptide or a fragment thereof. Alternatively, immunodetection and biochip technologies can be adopted for use with the Vip3 interacting polypeptide. A skilled artisan can readily employ numerous art-known techniques for determining whether a particular agent binds to a Vip3 interacting polypeptide.

Agents and cellular components can be further, or alternatively, tested for the ability to block the binding of a Vip3 toxin to a Vip3 interacting polypeptide. Alternatively, antibodies to the Vip3-toxin binding site or other agents that bind to the Vip3-toxin binding site on the Vip3 interacting polypeptide can be used in place of the Vip3 toxin.

Agents and cellular components can be further tested for the ability to modulate the activity of a Vip3 interacting polypeptide using a cell-free assay system or a cellular assay system. As the relevant activities of the Vip3 interacting polypeptide(s) become more defined, functional assays based on the identified activity can be employed.

As used herein, an agent is said to agonize Vip3 interacting activity when the agent causes an insecticidal or cytotoxic effect, e.g., the cells may themselves exhibit one of the indices of cell death, such as reduced thymidine uptake, slower increase in optical density of the culture, reduced exclusion of vital dyes (e.g., trypan blue), increased release of viability markers such as chromium and rubidium, and the like.

In certain embodiments of cell-based assays, the cells are contacted with the candidate toxic agent and the cytotoxic effect on metabolism or morphology is noted in the presence and absence of the candidate. The differential response between the toxin-treated cells and the cells absent the toxin is then noted. The strength of the toxin can be assessed by noting the strength of the response. The assay may be conducted directly as described above or competitively with known toxins. For example, one approach might be to measure the diminution in binding of labeled Vip3 toxin in the presence absence of the toxic agent candidate.

Agents that are assayed in the above method can be randomly selected or rationally selected or designed. As used herein, an agent is said to be randomly selected when the agent is chosen randomly without considering the specific sequences of the Vip3 interacting polypeptide or Vip3 toxin. An example of randomly selected agents is the use of a chemical library or a peptide combinatorial library, or a growth broth of an organism or plant extract. As used herein, an agent is said to be rationally selected or designed when the agent is chosen on a nonrandom basis that takes into account the sequence of the target site and/or its conformation in connection with the agent's action. Agents can be rationally selected or rationally designed by utilizing the peptide sequences that make up a Vip3 interacting polypeptide and Vip3 toxin. For example, a rationally selected peptide agent can be a peptide whose amino acid sequence is identical to a fragment of a Vip3 interacting polypeptide or Vip3. The agents tested in the methods of the present invention may include and not be limited to, peptides, small molecules, vitamin derivatives, or carbohydrates. A skilled artisan can readily recognize that there is no limit as to the structural nature of the agents used in the present screening method.

In addition to simply screening candidates, the screen can be used to devise modified forms of toxins which are more specific or less specific to particular classes of insects as desired. The ability to determine binding affinity (Ka and Kd) dissociation and association rates, and cytotoxic effects of a candidate allows quick, accurate and reproducible screening techniques for a large number of toxins and other ligands under identical conditions. Such information will facilitate the selection of the most effective toxins and ligands obtained from any desired host cell.

The following examples are intended solely to illustrate one or more preferred embodiments of the invention and are not to be construed as limiting the scope of the invention.

EXAMPLES

Example 1. Identification of Vip3A Interacting Proteins from an Sf9 Insect Cell Line Sf9 cells (*S. frugiperda*) were cultured at 26° C. in Grace's Insect Cell medium (Invitrogen) with 10% FBS (Sigma-Aldrich) and split into new medium by trypsinisation every 4-5 days. Fitly 15 cm dishes of cells were harvested at density of about 90% by scratching and collected by centrifugation at 500×g for 5 min. Cell pellets were washed 3 times with 50 ml of 1×PBS to remove trace amounts of FBS and medium components. The cell pellets were frozen at −80° C. overnight and resuspended the next day in 100 ml of extraction buffer, containing 0.5% NP40, 0.25 M NaCl, 50 mM HEPES, pH 7.4, 2 mM EDTA, 10% glycerol, phosphatase inhibitor (Sigma) and protease inhibitors (Roche). The solution was incubated overnight at 4° C. for extraction. The crude protein extract was separated from the unbroken cells and organelles by centrifugation at 34000×g for 30 min. Extracted proteins passed through either the control, non-bound agarose bead column or a Vip3A-bound agarose bead affinity column, prepared by the conjugation of trypsinized Vip3A to the agarose beads using a cross-linker kit (Thermo Fisher Scientific). The columns were washed extensively with extraction buffer and the binding proteins were desorbed from the column sequentially with an acidic buffer (100 mM glycine, pH2.2, 1M NaCl) and alkaline buffer (50 mM CAPS, pH 10; 1M NaCl). Proteins eluted by alkaline solution were analyzed on SDS-PAGE followed by silver staining (Thermo Fisher Scientific). Detected bands were cut out from the gel and analyzed by MS analysis. From this, ATP synthase α, ATP synthase β, and Hsc70 proteins from *S. frugiperda* (fall armyworm) (SEQ ID NO: 1, 2, and 3, respectively) were identified as interacting with trypsinized Vip3A.

Example 2. Detection of Interaction Between Vip3A and ATP Synthase by Western Blot Sf9 cells were cultured and crude protein was extracted and separated as described in Example 1. Proteins were bound to control beads or Vip3A beads as described in Example 1, Eluants and total crude protein extracted from Sf9 cells were each separated by SDS-PAGE and transferred onto PVDF membrane followed by detection with a monoclonal antibody against ATP synthase α (Mitoscience) that cross-reacts with fall armyworm ATP synthase at a dilution of 1:2000. ATP synthase α from the Sf9 cells was detected in the elution from the Vip3A affinity beads, but not to the control beads. Another analysis was performed using total proteins extracted from S2 (*Drosophila melanogaster*) cells transfected with either an empty plasmid or a plasmid expressing a flag-tagged ATP synthase β from *S. frugiperda*. The total protein extract was passed through either a column composed of non-bound agarose beads or trypsinized Vip3A bound to agarose beads. Binding proteins were eluted from the column using 2× SDS loading buffer. Following SDS-PAGE and transfer onto PVDF membrane, a western blot was performed using a HRP conjugated anti-Flag antibody (Sigma). The flag-tagged ATP synthase was detected in the elution from the Vip3A affinity beads, but not the control beads.

Example 3. Co-Immunoprecipitation of Vip3A from Insect Gut and Identification of Prohibitin as a Vip3A Interacting Polypeptide Gut material was isolated from *Helicoverpa zea* and *Manduca sexta* 2nd-4th in star larvae. Gut from each species was homogenized and sonicated at 4° C. in lysis buffer (PBS, 0.5% Triton-X100, 1× Roche complete protease inhibitor), the insoluble fraction was pelleted and the supernatant (gut extract) was saved. Beads were prepared by incubating Vip3A polyclonal antibodies with protein-A agarose in PBS for 30 minutes, followed by repeated washing of the beads with PBS. A portion of the Vip3A loaded beads were used to preclear the insect gut extract. To preclear, the loaded beads were added to the extract and rocked for 30 minutes. Beads were then pelleted and removed. For each insect, co-immunoprecipitate of Vip3A was performed as follows: Precleared gut extract was divided equally into 3 parts. Vip3A (full length) was added to one sample, trypsin activated Vip3A was added to the second sample, and nothing was added to the third sample. After rocking at room temperature for 60 minutes, an equal amount of Vip3A polyclonal antibodies bound to protein-A agarose (prepared as above for preclearing) was added to each sample and rocked at room temperature for 30 minutes. Beads were pelleted and the extract removed. The beads were washed multiple times in PBS, liquid was removed and beads were heated to 95° C. in SDS-PAGE loading buffer. The samples were then separated using SDS-PAGE and the gels were Coomassie stained. Bands that were unique to the Vip3A containing samples were excised for identification, and the corresponding regions in the control sample were also excised as negative controls.

Gel slices excised for ID were cut into 1 mm cubes. Pieces were washed with 100 mM $NH_4HCO_3$ buffer and dehydrated with acetonitrile (ACN, Merck) two times. Samples were then rehydrated with 100 mM $NH_4NCO_3$ buffer containing 10 mM DTT and then treated with 50 mM iodoacetamide in 100 mM $NH_4HCO_3$. Dehydration and rehydration were repeated two more times, and then dehydrated gel pieces were rehydrated with 50 mM $NH_4HCO_3$ containing 20 ng/μl trypsin (sequencing grade; Promega) and incubated for 12-16 hours at room temperature. Peptides were extracted with extraction buffer containing 50% ACN and 5% formic acid. The solution containing the extracted peptides was evaporated to less than half the volume in a vacuum centrifuge. Extracted peptides were separated by reverse phase on a capillary C18 picofrit 10 cm, 75 μm ID proteopep II column (New Objective) in 0.1% formic acid using acetonitrile as an eluent at 400 nl/min. Peptides were eluted on a nanospray source at 1.8-2.0 kV into a LCQ Deca XP-MAX ion trap mass spectrometer. Eluting peptides were recorded in positive ion mode and automatically subject to CID fragmentation by MS/MS. Data was then searched using MASCOT software against the MSDB database to identify the proteins. In both *H. zea* and *M. sexta* experiments, peptides matching "prohibitin 2" from *B. mori* were identified in trypsin activated Vip3A coIPs. The polypeptide sequences for each were subsequently determined (SEQ ID NO: 4 and 5, respectively) prohibitin-2 from *H. zea* and *M. sexta* were also used in subsequent experiments (SEQ NO: 6 and 7, respectively).

Example 4. Isolation of Vip3A Interacting Polypeptide Genes from Insect Larvae

To obtain clones of the identified Vip3A interacting polypeptides, the following Vip3 sensitive insect species were used for isolation of candidate interacting genes: *Bombyx mori* (ATP synthase α, ATP synthase β) *Spodoptera frugiperda* (ATP synthase α, ATP synthase β, Hsc70), *Helicoverpa zea* (prohibitin-1, prohibitin-2), and *Manduca sexta* (prohibitin-1, prohibitin-2). mRNA from insect larvae gut material was isolated using the Straight A mRNA kit (Novagen), and cDNAs were produced using the AccuScript High Fidelity First strand cDNA synthesis kit (Stratagem) according to manufacturer's instructions. Receptor genes were isolated by PCR amplification of corresponding sequences from first strand cDNAs. The primers for PCR amplifications of ATP synthase β, ATP synthase β, prohibitin-1, and prohibitin-2 were designed based on known sequences of corresponding genes from *Bombyx mori*. Compatible restriction sites were incorporated at the 5'ends of the primers to facilitate further subcloning of receptor candidates into the insect cell line cloning vector pIZT/V5-His (Invitrogen). The nucleic acids were subcloned into pIZT/V5-His in-frame with C-terminal V5-epitope and 6×His tags.

Example 5. Construction of a Yeast Surface-Displayed *Manduca sexta* cDNA Library Gut material from the 3rd instar of *Manduca sexta* larvae was collected by dissection and immediately frozen on dry ice. 250 mg of gut tissue was used for isolation of mRNA using an mRNA isolation kit (Stratagene) and following the manufacturer's protocol. Nine micrograms of isolated poly A+ RNA were used as a starting material for synthesis of cDNA by using the ZAP cDNA synthesis protocol (Stratagene). cDNA was directionally cloned into the pYD1 yeast surface display vector (Invitrogen) via. EcoRI and XhoI sites and transformed into *E. coli* XL10-Gold ultracompetent cells (Stratagene). After library amplification in *E. coli*, the mixed plasmid population (plasmid library) was isolated, transformed into the *Saccharomyces cerevisae* strain EBY100 (Invitrogen), and transformants were selected on minimal dextrose plates [0.67% yeast nitrogen base (YNB), 2% glucose, 0.01% leucine, 1.5% agar]. Greater than $2 \times 10^5$ transformants were pooled and harvested by resuspending the cells in YNB-CAA-Glu (0.67% YNB, 0.5% casamino acids, 2% glucose), aliquoting, and storing at −80° C. after the addition of 15% glycerol.

Example 6. Isolation of the Vip3 Binding Partner Serpin from *Manduca sexta* Yeast Surface-Displayed Library by Biopanning 300 μl of *Manduca sexta* expression library in yeast was inoculated into 20 ml of YNB-CAA-Glu media and grown at 30° C. for several hours (to an $OD_{600}$ of ~2). 5-10 ml of grown yeast culture was centrifuged and resuspended in 20 nil YNB-CAA-Gal (0.67% YNB, 0.5% casamino acids, 2% galactose) media. This culture was incubated at 20° C. for 24 hours to induce expression and to display library proteins on surface of yeast cells. Cells from 0.5 ml of yeast culture were harvested by centrifugation, resuspended in 1×PBS buffer supplemented with 0.1% BSA and 20 μg of trypsinised, biotinylated Vip1A (bVip3A/T) was added to the cell suspension. Cells were incubated with bVip3A/T for one hour at room temperature on a rotary wheel, before they were harvested, washed and resuspended in 0.5 ml of 1×PBS buffer. 50 μl of streptavidin-coated magnetic beads were added to the cell suspension and incubated on ice with occasional tube inversion for 10 minutes. A magnet was then applied to capture the beads and supernatant was removed. The magnetic beads with attached cells were cultured in 2 ml YNB-CAA-Glu media at 30° C. with shaking (300 rpm) for at least 2.5 hours to separate the captured cells from magnetic beads. Culture grown from beads was plated on large (15 cm diameter) minimal dextrose plates (0.67% YNB, 2% glucose, 0.01% leucine, 1.5% agar) and incubated at 30° C. for two days. All yeast colonies from plates were pooled into 1 ml of YNB-CAA-Glu media and stored at −80° C. with 20% glycerol. This material was subjected to another selection cycle described above and the whole selection ("panning") process was repeated 7 times. After the last selection, a mixed plasmid population was isolated from yeast cells and transformed into *E. coli*. plasmid DNA was isolated from individual *E. coli* colonies and the pYD1 plasmid inserts isolated from at least 20 clones were sequenced. After seven rounds of selection, nine out of twenty clones (45%) carried the gene for serpin. This level of enrichment after reiterative selection strongly indicates affinity of cell surface displayed serpin for bVip3A/T. In a negative control experiment (no incubation with bVip3A/T step was performed) no enrichment for serpin was observed (i.e., none out of twenty sequenced clones carried the serpin gene). The polypeptide sequence of serpin from *M. sexta* was determined (SEQ ID NO: 8).

Example 7. Vip3A Interacting Polypeptides Localized to Cell Surface in Cultured Insect Cells The pIZT vectors described in Example 4 comprising coding sequences for Vip3A interacting polypeptide candidates serpin, ATP synthase β, or Hsc70 were each transfected into Sf9 cells using Fugene HD reagent (Roche). Cells were incubated for 12 hours in Grace's Insect Cell medium without FBS and then for 48 hours in complete Grace's Insect Cell medium. Cells were trypsinized and transferred to confocal microscope dishes and allowed to grow for another 24 hrs followed by fixation with 4% paraformaldehyde for 20 minutes. The surfaces of the fixed cells were stained by a well-known non-permeabilization method with the FITC-conjugated anti-V5 antibody (Invitrogen) and mounted with anti-fade reagent with DAPI (Invitrogen). Fluorescent confocal microscope was used to check the distribution of the expressed protein in the SP) cells. ATP synthase β, serpin, and Hsc70 were each found to localize to the cell surface of Sf9 cells. DAPI was found to correctly localize to the nucleus for all transfected cells.

Example 8. Vip3A Interacting Polypeptide Render *Drosophila* S2 Cells Sensitive to Vip3A Treatment

*Drosophila* S2 cells were cultured at 26° C. with Schneider's insect cell medium (Invitrogen) with 10% heat inactivated FBS (Sigma) in semi-suspension and subcultured every 3-5 days. Two hours before the experiment, S2 cells were split into 6 well plates and serum medium with the attached cells was removed and replaced with fresh Schneider's medium with 10% FBS. Attached S2 cells were transfected with pIZT vectors (as described in example 4) comprising coding sequences for Hsc70, serpin, and ATP synthase α and β from *S. frugiperda*, using Fugene HD (Roche) for 12 hours. Additionally, S2 cells were co-transfected using similar methods with pIZT vectors expressing Hsc70 and ATP synthase α and β or Hsc70 and Serpin. All transfected or co-transfected cells were cultured for 48 hours. Then they were suspended and moved to confocal dishes followed by the treatment with 0 or 200 nM of active trypsinized Vip3A for 16 hours. Finally, cells were examined for morphological changes using fluorescent confocal microscopy. Results are shown below in Table 1:

TABLE 1

Vip3A interacting polypeptide confer cytotoxicity to *Drosophila* S2 cells treated with 200 nM Vip3A

|  | empty pIZT | Hsc70 | ATP synthase α and β | ATP synthase α and β and Hsc70 | serpin | serpin and Hsc70 |
|---|---|---|---|---|---|---|
| 0 nM Vip3A | no lysis | no lysis | no lysis | no lysis | no lysis | no lysis |
| 200 nM Vip3A | no lysis | no lysis | lysis | lysis | no lysis | lysis |

Cells transfected with ATP synthase α and β, with ATP synthase α and β and Hsc70, and with serpin and Hsc70, were observed to lyse in the presence of Vip3A.

Example 9: Detection of Interaction Between Vip3A and Vip3A Interacting Polypeptide by Far-Western Blot The pIZT vectors described in Example 4 comprising coding sequences for prohibitin-1 and prohibitin-2 from *H. zea*, ATP synthase α and β from *S. frugiperda*, or Hsc70 were each transfected into Sf9 cells using Fugene HD reagent (Roche) for 12 hr in Schneider's medium without FBS and continued to grow for 48 hours in complete Schneider's medium with 10% FBS and appropriate antibiotic selection. Sixty hours after transfection, the cells were collected by centrifugation, lysed with detergent buffer, and the proteins were separated from the remaining cellular extracts by centrifugation. Extracted proteins from the supernatant were then incubated with Anti-V5 conjugated beads, and the V5 tagged Vip3 interacting candidates were partially purified and enriched by elution from the beads with SDS loading buffer. The proteins were separated by SDS-PAGE and transferred onto PVDF membrane for Far-Western blot analysis. The membrane was incubated with biotin-labeled Vip3A and Streptavidin-HRP followed by enhanced chemiluminescence (ECL) detection. Vip3A bound to ATP synthase α and β as well as Hsc70. A similar Far-Western blot analysis was performed using biotin labeled Cry1Ab. The Vip3A interacting polypeptide were not observed to bind with Cry1Ab, although the cadherin positive control bound to Cry1Ab quite strongly.

Example 10: Interaction of Vip3A with Vip3A Interacting Polypeptides on Insect Cell Surface The pIZT vectors described in Example 4 comprising coding sequences of Vip3A interacting polypeptides ATP synthase α from *S. frugiperda*, ATP synthase β from *S. frugiperda*, or Hsc70 were each transfected into Sf9 cells using Fugene HD reagent (Roche) for 12 hr in Grace's Insect Cell medium without FBS and continued to grow for 48 hours in complete Grace's Insect Cell medium. The cells were then transferred to confocal microscope dishes and treated with 200 nM trypsinized Vip3A or V5-tagged Cry1Ab for 30 minutes. Cells were then co-stained with Vip3A conjugated to Fluor 546 (Invitrogen), and Anti-V5 Fluor 647 to visualize the location of the Vip3-interacting proteins using fluorescent confocal microscopy. Results indicate that ATP synthase and activated Vip3A co-localize at the cell surface. However, ATP synthase and activated Cry1Ab do not. Additionally, ATP synthase and activated Vip3A co-localize to the cell surface; however, ATP synthase and activated Cry1Ab do not.

Example 11: Dose Response of S2 Cells Transfected with Vip3A Interacting Polypeptides to Active Trypsinized Vip3A Treatment Co-transfection of *Drosophila* S2 cells was performed as in Example 8 using pIZT vectors expressing Hsc70, and both ATP synthase α and β from *S. frugiperda*; Hsc70 and serpin, Hsc70 and both prohibitin-1 and prohibitin-2 from *H. zea*; Hsc70, cadherin from *M. sexta*, and aminopeptidase-N (APN) from *M. sexta*; or empty pIZT vector. Following culturing for 48 hours, cells were suspended and transferred to confocal dishes, where they were treated with 0 to 800 nM of trypsinized Vip3A for 16 hours. Finally, cells were examined for morphological changes using fluorescent confocal microscopy. Cell death was determined by cell morphology and propidium iodide staining. The percentage of dead cells was calculated from each co-transfection and is presented in Table 2.

TABLE 2

S2 cell death in response to Vip3 and Vip3 binding partners

| | % of dead cells | | | | |
|---|---|---|---|---|---|
| Vip3A (nM) | Hsc70 + ATP synthases | Hsc70 + serpin | Hsc70 + prohibitins | Hsc70 + cadherin + APN | Empty Vector |
| 0 | 3.5 | 1.5 | 2.5 | 4 | 4 |
| 25 | 18 | 6 | 8 | 3 | 6 |
| 50 | 37 | 17 | 19 | 7 | 7 |
| 100 | 64 | 34 | 33 | 6 | 6 |
| 200 | 92 | 64 | 56 | 9 | 9 |
| 400 | 98 | 81 | 87 | 10 | 7 |
| 800 | 98.5 | 96 | 97 | 8 | 8 |

As expected, cell death is minimal in the samples transfected with Hsc70 and cadherin and APN, the latter two of which interact with Cry1Ab, in the samples transfected with empty vector, or in samples treated with 0 nM trypsinized Vip3A. Cells co-transfected with Vip3 binding partners showed increasing cell death in the presence of increasing amounts of Vip3A, suggesting the Vip3 interacting proteins play a role in cell death in the presence of Vip3.

Example 12: Knock Down of ATP Synthase and Hsc70 in Sf9 Cells Reduces Vip3A Toxicity Sf9 cells were maintained in Grace's Insect Medium (Invitrogen) plus 10% FBS and split into 48 well plates the day before the transfection at 85% confluence. Cells were transfected with 0.5 µg of dsRNA targeting HSC70 or ATP synthase α and β (SEQ ID NO: 9, 10, and 11, respectively) or GFP (as a negative control) by applying 2.5 µl of TransMessenger reagent (Qiagen) in plain Grace's Insect Medium for 5 hr and replaced the transfection complex with complete Grace's Insect Medium plus 10% FBS for 48 hours according to manufacturer's instructions. Cells were then treated with 200 nM trypsinized Vip3A in plain Grace's Insect Medium without FBS for 48 hours after transfection. Cell viability was measured by adding 50 µl of Cell-Titer Glow solution (Promega) and recording the luminescence with a Luminometer (Beckman). Results are shown in Table 3, expressed as a percent reduction of cell viability.

TABLE 3

Vip3 toxicity in Sf9 cells following silencing of Vip3 interacting polypeptides

| Hsc70 | ATP synthase β | ATP synthase α | ATP synthase α + β | GFP |
|---|---|---|---|---|
| 17.074 | 22.654 | 0.990 | 0.986 | 30.055 |

As shown in Table 2, the toxicity of Vip3 in Sf9 cells with Hsc70 or one or both of ATP synthases α and β is significantly reduced compared to the GFP control, where none of the Vip3 interacting proteins have their expression silenced.

Example 13: RNAi-Based Silencing of Hsc70, ATP Synthase α, and ATP Synthase β of *S. frugiperda* Reduces Vip3A Toxicity Fall armyworm (*Spodoptera frugiperda*) eggs were purchased from French Agricultural Research. In, (Lamberton, Min.), Eggs were hatched at 28° C. The neonate larvae were employed as testing insects. Insects were maintained on a standard artificial diet supplemented with Cefotaxme and Spectinomycin at 0.625 mg/ml and 0.375 mg/ml, respectively. dsRNA to Hsc70 and ATP synthase α or β (SEQ ID NO: 9, 10, and respectively) was suspended in water and overlaid onto the surface of artificial diet in each well of a 128-well plate at 100 ng/cm$^2$. Individual FAW larvae were added onto the diet of each well, for a total sample size of 128 insect larvae. Larvae were transferred after three days into individual wells of 128-well plates containing the commercial diet "Multiple Species" from Southland Product Inc. (Lake Village, Ark.), supplemented with Cefotaxme and Spectinomycin at 0.625 mg/ml and 0.375 mg/ml, respectively, and overlaid with Vip3A protein at 100 ng/cm$^2$. Mortality was observed using microscopy and recorded daily. A summary of the results is shown in Table 4.

TABLE 4

The susceptibility of RNAi-pretreated FAW larvae to Vip3A toxin on artificial diet supplemented with Vip3A at 100 ng/cm$^2$

| dsRNA for Target Gene | Mortality (%) | | |
|---|---|---|---|
| | Day 2 | Day 6 | Day 10 |
| Hsc70 | 0.00 | 0.00 | 6.25 |
| ATP synthase α | 12.50 | 12.50 | 37.50 |
| ATP synthase β | 0.00 | 15.38 | 53.85 |
| ZsGreen (negative control) | 7.16 | 37.50 | 56.25 |

Example 14: Pull-Down Studies

BT strain (C0548) from China collection harbors a variety of Bt proteins including both Cry proteins and Vip proteins, totally about 20 insecticidal proteins based on the genetic sequence analysis. C0548 was cultured in T3 medium for 5 days. The bacteria were separated from the supernatant by centrifugation. Bacterial pellets were suspended and processed with Microfluidics, Western blot analysis confirmed that at least Vip3A and Cry II are expressed in the Bt strain and were successfully extracted.

Purified Vip3A interactors, e.g. ATP synthase (α and/or ß), HSC 70, prohibitin (prohibitin-1 and/or prohibitin-2) and/or serpin are immobilized onto agarose beads and used to pull down Vip3A and other non-Vip3A proteins. In one study, prohibitin proteins (prohibitin-1 and prohibitin-1) were covalently linked to agarose beads. Empty (control) beads or beads conjugated with the prohibitin proteins were incubated with C0548 extract, followed by multiple washings. Proteins binding to the beads were recovered by SDS-PAGE loading buffer. Western blot analysis performed with anti-Vip3A antibody showed that the Vip3A protein was successfully pulled down by prohibitin (prohibitin-1 and prohibitin-2) beads. The samples were further analyzed by mass spectrometry for the presence of other Bt proteins in the eluted sample.

Example 15: Method for Screening Insecticidal Proteins

*Bacillus thuringiensis* (Bt) strain C0576 and AB88 are cultured in T3 medium for 5 days. The bacteria are separated from the supernatant by centrifugation. The intracellular total proteins are extracted by sonication of the suspended bacterial pellet. The secreted fraction of total proteins in the supernatant of the culture is precipitated with $(NH_4)_2SO_4$ at 100% saturation.

*Drosophila* S2 cells are transfected with Hsc70, ATP synthase (e.g., ATP synthase α and/or ß) and/or prohibitin-1 and/or prohibitin-2 in the pIZT expression plasmid and cells are selected on Zeocin media for one month. Cell lines stably expressing V5-tagged Hsc70, ATP synthase (α and/or ß), and/or prohibitin (-1 and/or -2) are obtained and continuously cultured in S2 cells. Cultured stable cell lines are collected by centrifugation and extracted by detergent buffer. Extracted proteins from S2 cells are mixed with intracellular (or secreted) proteins from Bt strains. Vip3A interacting proteins are coimmunoprecipitated with Vip3A protein by agarose beads conjugated with anti-V5 antibody and eluted with glycine buffer, pH2.2, Eluted samples are analyzed by silver staining and protein bands identified by mass spectrometry.

Example 16: Cell Based Method for Screening Novel Insecticidal Proteins and Compounds Expression cassettes on the pIZT expression vector encoding Vip3A interacting polypeptides are transfected into an insect cell line (S2 or other insect cell lines). A negative control of the pIZT empty vector is also transfected into the same insect cell line. Successfully transfected insect cells are selected for on Zeocin media for one month. The isogenic stable cell lines are used to screen agents, including proteins from biological extracts. Agents which provide a differential response in the presence or absence of the Vip3A interacting polypeptide(s) are identified. These agents decrease the viability of insect cells expressing Vip3A interacting peptide (s), but do not decrease the viability of insect cells which express the empty pIZT vector.

Example 17: Identification of Polypeptides that Interact with Other Vip3 Proteins The worker of ordinary skill can identify additional Vip3 interacting polypeptides using other members of the Vip3 family based on the studies and guidance provided herein. Examples 1, 3, and 5 disclose illustrative methods of identifying Vip3A interacting polypeptides; however, similar methods may be used to identify any polypeptides that interact with any Vip3 (e.g., Vip3D or Vip3E). For example, in representative embodiments, such methods employ insect extracts and materials from a corresponding susceptible insect. To illustrate, Vip3E interacting proteins may be identified using Vip3E isolated protein and extracts from *Ostrinia nubilalis* (European corn borer) following methods similar to those of Examples 1, 3, and 5.

Although the foregoing invention has been described in some detail by way of illustration and example for purposes of clarity of understanding, it will be obvious that certain changes and modifications may be practiced within the scope of the list of the foregoing embodiments and the appended claims.

What is claimed is:

1. An expression cassette comprising a promoter operably linked to a heterologous polynucleotide sequence that encodes a Vip3A-interacting protein from a *Spodoptera frugiperda* insect that is susceptible to a Vip3A insecticidal protein, wherein the Vip3A-interacting protein is a heat shock cognate 70 (Hsc70) protein comprising the amino acid sequence of SEQ ID NO: 3.

2. The expression cassette of claim 1, wherein the promoter is functional in an insect cell.

3. The expression cassette of claim 2, wherein the insect cell is a *Spodoptera frugiperda* cell.

4. The expression cassette of claim 3, wherein the *Spodoptera frugiperda* cell is an Sf9 cell.

5. The expression cassette of claim 2, wherein the insect cell is a *Drosophila melanogaster* cell.

6. The expression cassette of claim 5, wherein the *Drosophila melanogaster* cell is an S2 cell.

7. A cultured insect cell comprising the expression cassette of claim 1.

8. The cultured insect cell of claim 7, wherein the cultured insect cell is a *Spodoptera frugiperda* cell.

9. The cultured insect cell of claim 8, wherein the *Spodoptera frugiperda* cell is an Sf9 cell.

10. The cultured insect cell of claim 7, wherein the cultured insect cell is a *Drosophila melanogaster* cell.

11. The cultured insect cell of claim 10, wherein the *Drosophila melanogaster* cell is an S2 cell.

12. A cultured insect cell line comprising the cultured insect cell of claim 7.

13. The cultured insect cell line of claim 12, wherein the cultured insect cell line is a *Spodoptera frugiperda* Sf9 cell line.

14. The cultured insect cell line of claim 12, wherein the cultured insect cell line is a *Drosophila melanogaster* S2 cell line.

15. A method of producing a Vip3A-interacting protein comprising culturing an insect cell comprising the expression cassette of claim 1 to thereby produce the Vip3A-interacting protein, wherein the Vip3A-interacting protein is a Hsc70 protein.

* * * * *